US011877733B2

(12) United States Patent
Nicholas et al.

(10) Patent No.: US 11,877,733 B2
(45) Date of Patent: Jan. 23, 2024

(54) ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF

(71) Applicant: Covidien LP, Mansfield, MA (US)

(72) Inventors: David Nicholas, Trumbull, CT (US); Russell Pribanic, Roxbury, CT (US)

(73) Assignee: COVIDIEN LP, Mansfield, MA (US)

( * ) Notice: Subject to any disclaimer, the term of this patent is extended or adjusted under 35 U.S.C. 154(b) by 15 days.

(21) Appl. No.: 17/716,018

(22) Filed: Apr. 8, 2022

(65) Prior Publication Data
US 2022/0225974 A1 Jul. 21, 2022

Related U.S. Application Data

(63) Continuation of application No. 16/295,391, filed on Mar. 7, 2019, now Pat. No. 11,298,114, which is a
(Continued)

(51) Int. Cl.
*A61B 17/00* (2006.01)
*A61B 17/072* (2006.01)
*A61B 17/29* (2006.01)

(52) U.S. Cl.
CPC ........ *A61B 17/00* (2013.01); *A61B 17/07207* (2013.01); *A61B 2017/0069* (2013.01);
(Continued)

(58) Field of Classification Search
CPC . A61B 17/00; A61B 17/29; A61B 2017/2927; A61B 2017/0046;
(Continued)

(56) References Cited

U.S. PATENT DOCUMENTS

| 677,869 A * | 7/1901 | Kinsler | F16D 3/36 |
| | | | 464/139 |
| 1,287,778 A * | 12/1918 | Sponsel | F16D 3/48 |
| | | | 464/138 |

(Continued)

FOREIGN PATENT DOCUMENTS

| CN | 101011291 A | 8/2007 |
| CN | 101283924 A | 10/2008 |

(Continued)

OTHER PUBLICATIONS

Australian Examination Report dated Sep. 26, 2019, issued in AU Appln. No. 2016201148.
(Continued)

*Primary Examiner* — Gloria R Weeks
*Assistant Examiner* — Mobeen Ahmed
(74) *Attorney, Agent, or Firm* — Carter, DeLuca & Farrell, LLP

(57) ABSTRACT

The present disclosure relates to adapter assemblies for use with and to electrically and mechanically interconnect electromechanical surgical devices and surgical loading units, and to surgical systems including handheld electromechanical surgical devices and adapter assemblies for connecting surgical loading units to the handheld electromechanical surgical devices.

14 Claims, 19 Drawing Sheets

Related U.S. Application Data continuation of application No. 14/991,401, filed on Jan. 8, 2016, now Pat. No. 10,226,239.

(60) Provisional application No. 62/145,794, filed on Apr. 10, 2015.

(52) U.S. Cl.
CPC .............. *A61B 2017/00398* (2013.01); *A61B 2017/00473* (2013.01); *A61B 2017/00477* (2013.01); *A61B 2017/07214* (2013.01); *A61B 2017/2927* (2013.01)

(58) Field of Classification Search
CPC .... A61B 2017/00323; A61B 2017/003; A61B 2017/00367
USPC .......................... 464/136, 117, 139, 140, 152
See application file for complete search history.

(56) References Cited

U.S. PATENT DOCUMENTS

| | | | |
|---|---|---|---|
| 1,886,847 | A * | 11/1932 | Tenney ...................... F16D 3/24 464/143 |
| 1,913,045 | A * | 6/1933 | Wood ........................ F16D 3/36 464/139 |
| 2,777,340 | A | 1/1957 | Hettwer et al. |
| 2,879,651 | A * | 3/1959 | Leto ........................... F16D 3/16 464/139 |
| 2,957,353 | A | 10/1960 | Babacz |
| 3,111,328 | A | 11/1963 | Di Rito et al. |
| 3,310,959 | A * | 3/1967 | Sheppard .................. F16D 3/36 403/220 |
| 3,695,058 | A | 10/1972 | Keith, Jr. |
| 3,734,515 | A | 5/1973 | Dudek |
| 3,759,336 | A | 9/1973 | Marcovitz et al. |
| 3,943,778 | A * | 3/1976 | Wyse ....................... F16D 3/005 29/445 |
| 4,162,399 | A | 7/1979 | Hudson |
| 4,606,343 | A | 8/1986 | Conta et al. |
| 4,705,038 | A | 11/1987 | Sjostrom et al. |
| 4,722,685 | A | 2/1988 | de Estrada et al. |
| 4,722,716 | A * | 2/1988 | Engler ...................... F16D 3/36 464/139 |
| 4,823,807 | A | 4/1989 | Russell et al. |
| 4,846,763 | A * | 7/1989 | Di Stefano ............... F16D 3/38 464/139 |
| 4,874,181 | A | 10/1989 | Hsu |
| 5,129,118 | A | 7/1992 | Walmesley |
| 5,129,570 | A | 7/1992 | Schulze et al. |
| 5,152,744 | A | 10/1992 | Krause et al. |
| 5,301,061 | A | 4/1994 | Nakada et al. |
| 5,312,023 | A | 5/1994 | Green et al. |
| 5,326,013 | A | 7/1994 | Green et al. |
| 5,350,355 | A | 9/1994 | Sklar |
| 5,383,874 | A | 1/1995 | Jackson et al. |
| 5,383,880 | A | 1/1995 | Hooven |
| 5,389,098 | A | 2/1995 | Tsuruta et al. |
| 5,395,033 | A | 3/1995 | Byrne et al. |
| 5,400,267 | A | 3/1995 | Denen et al. |
| 5,411,508 | A | 5/1995 | Bessler et al. |
| 5,413,267 | A | 5/1995 | Solyntjes et al. |
| 5,427,087 | A | 6/1995 | Ito et al. |
| 5,433,721 | A | 7/1995 | Hooven et al. |
| 5,467,911 | A | 11/1995 | Tsuruta et al. |
| 5,476,379 | A | 12/1995 | Disel |
| 5,487,499 | A | 1/1996 | Sorrentino et al. |
| 5,518,163 | A | 5/1996 | Hooven |
| 5,518,164 | A | 5/1996 | Hooven |
| 5,526,822 | A | 6/1996 | Burbank et al. |
| 5,529,235 | A | 6/1996 | Boiarski et al. |
| 5,535,934 | A | 7/1996 | Boiarski et al. |
| 5,535,937 | A | 7/1996 | Boiarski et al. |
| 5,540,375 | A | 7/1996 | Bolanos et al. |
| 5,540,706 | A | 7/1996 | Aust et al. |
| 5,542,594 | A | 8/1996 | McKean et al. |
| 5,549,637 | A | 8/1996 | Crainich |
| 5,553,675 | A | 9/1996 | Pitzen et al. |
| 5,562,239 | A | 10/1996 | Boiarski et al. |
| 5,564,615 | A | 10/1996 | Bishop et al. |
| 5,609,560 | A | 3/1997 | Ichikawa et al. |
| 5,626,587 | A | 5/1997 | Bishop et al. |
| 5,632,432 | A | 5/1997 | Schulze et al. |
| 5,645,209 | A | 7/1997 | Green et al. |
| 5,647,526 | A * | 7/1997 | Green ............... A61B 17/07207 227/176.1 |
| 5,653,374 | A | 8/1997 | Young et al. |
| 5,658,300 | A | 8/1997 | Bito et al. |
| 5,662,662 | A | 9/1997 | Bishop et al. |
| 5,667,517 | A | 9/1997 | Hooven |
| 5,693,042 | A | 12/1997 | Boiarski et al. |
| 5,704,534 | A | 1/1998 | Huitema et al. |
| 5,713,505 | A | 2/1998 | Huitema |
| 5,716,278 | A * | 2/1998 | Krude ...................... F16D 3/224 464/145 |
| 5,762,603 | A | 6/1998 | Thompson |
| 5,779,130 | A | 7/1998 | Alesi et al. |
| 5,782,396 | A | 7/1998 | Mastri et al. |
| 5,782,397 | A | 7/1998 | Koukline |
| 5,792,573 | A | 8/1998 | Pitzen et al. |
| 5,797,536 | A | 8/1998 | Smith et al. |
| 5,820,009 | A | 10/1998 | Melling et al. |
| 5,863,159 | A | 1/1999 | Lasko |
| 5,908,427 | A | 6/1999 | McKean et al. |
| 5,954,259 | A | 9/1999 | Viola et al. |
| 5,964,774 | A | 10/1999 | McKean et al. |
| 5,993,454 | A | 11/1999 | Longo |
| 6,010,054 | A | 1/2000 | Johnson et al. |
| 6,017,354 | A | 1/2000 | Culp et al. |
| 6,032,849 | A | 3/2000 | Mastri et al. |
| 6,045,560 | A | 4/2000 | McKean et al. |
| 6,090,123 | A | 7/2000 | Culp et al. |
| 6,126,651 | A | 10/2000 | Mayer |
| 6,129,547 | A | 10/2000 | Cise et al. |
| 6,165,169 | A | 12/2000 | Panescu et al. |
| 6,239,732 | B1 | 5/2001 | Cusey |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,302,311 | B1 | 10/2001 | Adams et al. |
| 6,315,184 | B1 | 11/2001 | Whitman |
| 6,321,855 | B1 | 11/2001 | Barnes |
| 6,329,778 | B1 | 12/2001 | Culp et al. |
| 6,343,731 | B1 | 2/2002 | Adams et al. |
| 6,348,061 | B1 | 2/2002 | Whitman |
| 6,368,324 | B1 | 4/2002 | Dinger et al. |
| 6,371,909 | B1 | 4/2002 | Hoeg et al. |
| 6,434,507 | B1 | 8/2002 | Clayton et al. |
| 6,443,973 | B1 | 9/2002 | Whitman |
| 6,461,372 | B1 | 10/2002 | Jensen et al. |
| 6,488,197 | B1 | 12/2002 | Whitman |
| 6,491,201 | B1 | 12/2002 | Whitman |
| 6,533,157 | B1 | 3/2003 | Whitman |
| 6,537,280 | B2 | 3/2003 | Dinger et al. |
| 6,610,066 | B2 | 8/2003 | Dinger et al. |
| 6,611,793 | B1 | 8/2003 | Burnside et al. |
| 6,645,218 | B1 | 11/2003 | Cassidy et al. |
| 6,654,999 | B2 | 12/2003 | Stoddard et al. |
| 6,698,643 | B2 | 3/2004 | Whitman |
| 6,699,177 | B1 | 3/2004 | Wang et al. |
| 6,716,233 | B1 | 4/2004 | Whitman |
| 6,743,240 | B2 | 6/2004 | Smith et al. |
| 6,783,533 | B2 | 8/2004 | Green et al. |
| 6,792,390 | B1 | 9/2004 | Burnside et al. |
| 6,793,652 | B1 | 9/2004 | Whitman et al. |
| 6,817,508 | B1 | 11/2004 | Racenet et al. |
| 6,830,174 | B2 * | 12/2004 | Hillstead .......... A61B 17/07207 227/175.1 |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,860,892 | B1 | 3/2005 | Tanaka et al. |

(56) References Cited

U.S. PATENT DOCUMENTS

| | | |
|---|---|---|
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 * | 9/2006 | Wales .............. A61B 17/07207 227/180.1 |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |

(56) References Cited

U.S. PATENT DOCUMENTS

| | | |
|---|---|---|
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,125,662 B2* | 9/2015 | Shelton, IV ............ A61B 34/37 |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,492,146 B2 | 11/2016 | Kostrzewski et al. |
| 10,080,552 B2 | 9/2018 | Nicholas et al. |
| 10,226,239 B2 | 3/2019 | Nicholas et al. |
| 10,226,254 B2* | 3/2019 | Cabrera ............ A61B 17/1155 |
| 10,499,890 B2 | 12/2019 | Shelton, IV et al. |
| 10,588,629 B2 | 3/2020 | Malinouskas et al. |
| 11,298,114 B2 | 4/2022 | Nicholas et al. |
| 2005/0043718 A1* | 2/2005 | Madhani ................ A61B 34/76 606/1 |
| 2005/0079917 A1* | 4/2005 | Menosky ................ F16C 17/08 464/128 |
| 2005/0125027 A1 | 6/2005 | Knodel et al. |
| 2005/0131442 A1 | 6/2005 | Yachia et al. |
| 2006/0095074 A1* | 5/2006 | Lee ........................ A61B 17/29 606/205 |
| 2006/0111210 A1* | 5/2006 | Hinman ................. A61B 17/29 474/206 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0106317 A1* | 5/2007 | Shelton, IV ......... A61B 17/072 606/170 |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0179476 A1* | 8/2007 | Shelton, IV ....... A61B 17/2812 606/1 |
| 2007/0221701 A1* | 9/2007 | Ortiz ................. A61B 1/00042 227/175.1 |
| 2007/0270784 A1 | 11/2007 | Smith et al. |
| 2007/0299387 A1* | 12/2007 | Williams ........... A61B 1/00052 600/149 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1* | 2/2008 | Shelton ............ A61B 17/07207 227/176.1 |
| 2008/0046000 A1* | 2/2008 | Lee ........................ A61B 17/29 606/205 |
| 2008/0058801 A1 | 3/2008 | Taylor et al. |
| 2008/0064921 A1* | 3/2008 | Larkin ............... A61B 1/00193 128/898 |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1* | 12/2008 | Shelton ............ A61B 17/07207 227/175.1 |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0022837 A1* | 1/2010 | Ishiguro ................ A61B 17/29 600/146 |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0320252 A1* | 12/2010 | Viola ................... A61B 17/068 227/176.1 |
| 2011/0071508 A1* | 3/2011 | Duval ................ A61B 1/00087 606/1 |
| 2011/0077673 A1 | 3/2011 | Grubac et al. |
| 2011/0118709 A1* | 5/2011 | Burbank .................. F16D 3/26 606/1 |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0184459 A1* | 7/2011 | Malkowski ........ A61B 17/2909 606/206 |
| 2011/0204119 A1 | 8/2011 | McCuen |
| 2011/0218522 A1 | 9/2011 | Whitman |
| 2011/0230894 A1* | 9/2011 | Simaan ............... A61B 1/00183 606/130 |
| 2011/0276057 A1 | 11/2011 | Conlon et al. |
| 2011/0277776 A1 | 11/2011 | McGrogan |
| 2011/0290854 A1 | 12/2011 | Timm et al. |
| 2011/0295242 A1* | 12/2011 | Spivey ............ A61B 17/07207 606/1 |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253326 A1* | 10/2012 | Kleyman ............... A61B 34/30 606/1 |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |

(56) References Cited

U.S. PATENT DOCUMENTS

| | | | |
|---|---|---|---|
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0098966 A1* | 4/2013 | Kostrzewski | A61B 17/07207 606/1 |
| 2013/0098968 A1* | 4/2013 | Aranyi | A61B 90/94 227/177.1 |
| 2013/0098969 A1 | 4/2013 | Scirica et al. | |
| 2013/0105545 A1* | 5/2013 | Burbank | A61B 17/07207 227/175.1 |
| 2013/0172858 A1* | 7/2013 | Doyle | A61B 17/00 606/1 |
| 2013/0178838 A1 | 7/2013 | Malkowski | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0317522 A1* | 11/2013 | Nishizawa | A61B 17/3423 606/130 |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0001234 A1* | 1/2014 | Shelton, IV | A61B 17/072 74/25 |
| 2014/0005653 A1* | 1/2014 | Shelton, IV | A61B 18/14 606/205 |
| 2014/0005662 A1 | 1/2014 | Shelton, IV | |
| 2014/0005679 A1* | 1/2014 | Shelton, IV | A61B 17/07207 606/130 |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0094782 A1* | 4/2014 | Jeong | A61B 17/29 606/1 |
| 2014/0110455 A1 | 4/2014 | Ingmanson et al. | |
| 2014/0188159 A1 | 7/2014 | Steege | |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0236173 A1 | 8/2014 | Scirica et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0365235 A1 | 12/2014 | DeBoer et al. | |
| 2014/0373652 A1 | 12/2014 | Zergiebel et al. | |
| 2015/0014392 A1 | 1/2015 | Williams et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0112381 A1 | 4/2015 | Richard | |
| 2015/0122870 A1 | 5/2015 | Zemlok et al. | |
| 2015/0133224 A1 | 5/2015 | Whitman et al. | |
| 2015/0133957 A1 | 5/2015 | Kostrzewski | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0067000 A1* | 3/2016 | Johnston | A61B 34/30 606/130 |
| 2016/0095585 A1 | 4/2016 | Zergiebel et al. | |
| 2016/0095596 A1 | 4/2016 | Scirica et al. | |
| 2016/0106406 A1* | 4/2016 | Cabrera | A61B 17/1155 606/1 |
| 2016/0113648 A1 | 4/2016 | Zergiebel et al. | |
| 2016/0113649 A1 | 4/2016 | Zergiebel et al. | |
| 2016/0184040 A1* | 6/2016 | Sholev | A61B 17/00234 606/130 |
| 2016/0192915 A1* | 7/2016 | Papenfuss | A61B 17/00234 606/130 |
| 2016/0296216 A1* | 10/2016 | Nicholas | A61B 17/00 |
| 2017/0095305 A1 | 4/2017 | Danitz | |
| 2017/0095922 A1* | 4/2017 | Licht | A61B 34/76 |
| 2017/0135695 A1* | 5/2017 | Shelton, IV | A61B 17/105 |

FOREIGN PATENT DOCUMENTS

| | | |
|---|---|---|
| CN | 101401737 A | 4/2009 |
| CN | 101912285 A | 12/2010 |
| CN | 103371858 A | 10/2013 |
| EP | 1693018 A1 | 8/2006 |
| EP | 2772214 A2 | 9/2014 |
| JP | 2012522554 A | 9/2012 |
| JP | 2013215578 A | 10/2013 |
| WO | 2009039506 A1 | 3/2009 |

OTHER PUBLICATIONS

Japanese Office Action dated Nov. 21, 2019 corresponding to counterpart Patent Application JP 2016-067701.
Chinese First Office Action dated Oct. 9, 2019 corresponding to counterpart Patent Application CN 201610217764.5.
Chinese Office Action issued in corresponding Chinese Application No. 202010358241.9 dated Feb. 28, 2023, 20 pages.

* cited by examiner

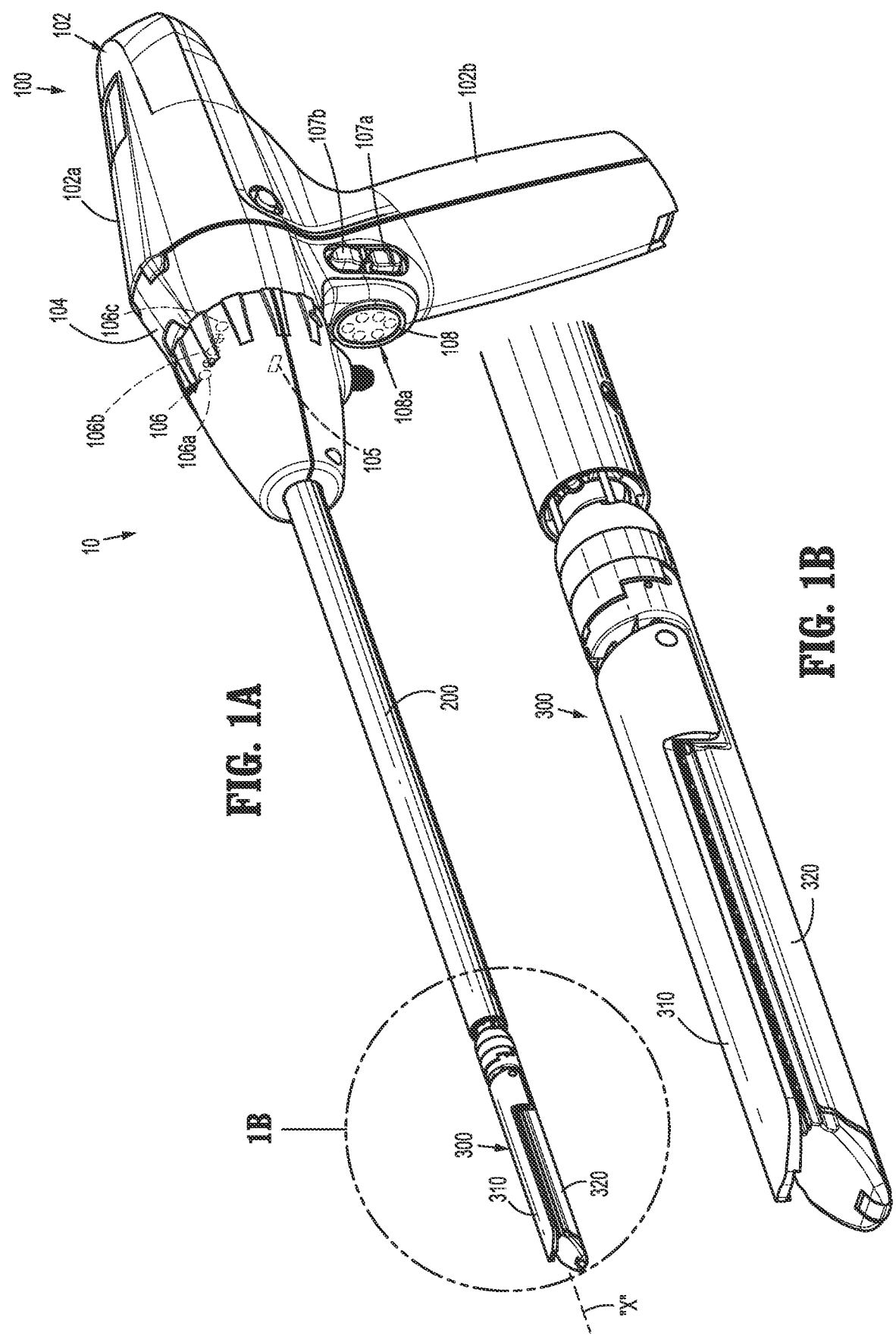

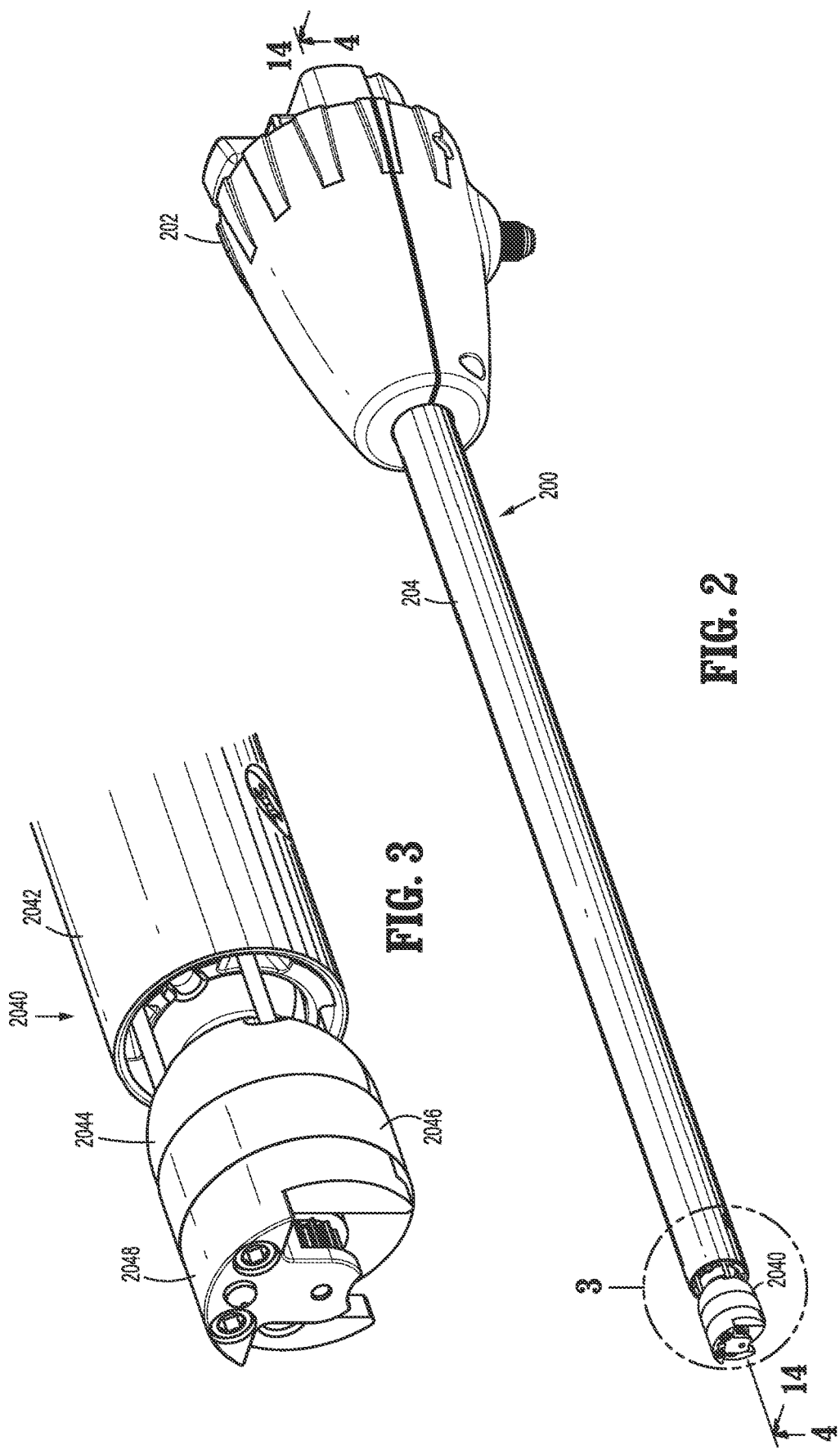

ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF

CROSS-REFERENCE TO RELATED APPLICATIONS

This application is a continuation of U.S. patent application Ser. No. 16/295,391, filed Mar. 7, 2019, now U.S. Pat. No. 11,298,114, which is a continuation of U.S. patent application Ser. No. 14/991,401, filed Jan. 8, 2016, now U.S. Pat. No. 10,226,239, which claims the benefit of and priority to U.S. Provisional Patent Application No. 62/145,794, filed Apr. 10, 2015, the entire disclosure of each of which is incorporated by reference herein.

TECHNICAL FIELD

The present disclosure relates to adapter assemblies for use in surgical systems. More specifically, the present disclosure relates to adapter assemblies for use with, and to electrically and mechanically interconnect, electromechanical surgical devices and surgical loading units, and to surgical systems including handheld electromechanical surgical devices and adapter assemblies for connecting surgical loading units to the handheld electromechanical surgical devices.

BACKGROUND

Surgical device manufacturers have developed product lines with proprietary powered drive systems for operating and/or manipulating the surgical device. In instances the surgical devices include a powered handle assembly, which is reusable or disposable, and a disposable end effector or the like that is selectively connected to the powered handle assembly prior to use and then disconnected from the end effector following use in order to be disposed of or in some instances sterilized for re-use.

Many of the existing end effectors for use with many of the existing powered surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. Many of these adapter and/or adapter assemblies are complex devices including many parts and requiring extensive labor to assemble. Accordingly, a need exists to develop adapters and/or adapter assemblies that incorporate fewer parts, are less labor intensive to assemble, and are ultimately more economical to manufacture.

SUMMARY

The present disclosure relates to adapter assemblies for use with and to electrically and mechanically interconnect electromechanical surgical devices and surgical loading units, and to surgical systems including handheld electromechanical surgical devices and adapter assemblies for connecting surgical loading units to the handheld electromechanical surgical devices. Embodiments of the adapter assemblies of the present disclosure have a gimbal and two universal joints for providing the surgical loading units with omnidirectional degrees of freedom. The resulting articulation angle of the surgical loading units relative to the handheld electromechanical surgical device can result in improved access to tissue within a surgical site.

According to an aspect of the present disclosure, an adapter assembly for selectively interconnecting a surgical loading unit that is configured to perform a function and a surgical device that is configured to actuate the surgical loading unit, the surgical loading unit including an axially translatable drive member, and the surgical device including one or more rotatable drive shafts, includes a housing, an outer tube, an articulation assembly, and a firing assembly.

The housing is configured and adapted for connection with the surgical device and to be in operative communication with a rotatable drive shaft rotatable drive shafts of the surgical device. The outer tube defines a longitudinal axis and has a proximal end supported by the housing and a distal end portion configured and adapted for connection with the surgical loading unit. The distal end portion of the outer tube is in operative communication with the axially translatable drive member of the surgical loading unit.

The adapter assembly includes an articulation assembly including a gimbal supported in the distal end portion of the outer tube and a plurality of threaded sleeves supported in the housing. The plurality of threaded sleeves is coupled to the gimbal by at least one cable. The firing assembly includes a firing shaft supported within the housing and the outer tube. The firing shaft includes at least one universal joint. Rotation of at least one of the plurality of rotatable drive shafts of the surgical device translates at least two of the plurality of threaded sleeves to articulate the gimbal relative to the longitudinal axis of the outer tube with the at least one cable. Articulation of the gimbal articulates the at least one universal joint of the firing shaft and the surgical loading unit about the distal end portion of the outer tube.

In embodiments, the firing shaft includes a proximal end configured and adapted to couple to at least one of the plurality of rotatable drive shafts of the surgical device, and a distal end configured and adapted to couple to the axially translatable drive member of the surgical loading unit to enable firing of the surgical loading unit. The at least one universal joint is positioned between the proximal and distal ends of the firing shaft. In some embodiments, the firing shaft is configured and adapted to transmit a rotational force through the gimbal to effectuate axial translation of the axially translatable drive member and to fire the surgical loading unit.

The firing shaft may include a proximal firing shaft, a central tube, and a distal firing shaft. In embodiments, the proximal firing shaft and the central tube are connected at a proximal universal joint of the at least one universal joint such that the central tube is movable relative to the proximal firing shaft. In some embodiments, the proximal firing shaft includes a pair of opposed distal tabs that form a first hinge of the proximal universal joint and the central tube includes a pair of opposed proximal tabs that form a second hinge of the proximal universal joint. The first and second hinges of the proximal universal joint are interconnected by a proximal bearing assembly. In certain embodiments, the proximal bearing assembly includes a plurality of outer arcuate surfaces. Each outer arcuate surface is disposed in an inner arcuate surface defined in each of the pair of opposed distal tabs of the proximal firing shaft and the pair of opposed proximal tabs of the central tube.

In embodiments, the central tube and the distal firing shaft are connected at a distal universal joint of the at least one universal joint such that the distal firing shaft is movable relative to the central tube. In some embodiments, the central tube includes a pair of opposed distal tabs that form a first hinge of the distal universal joint and the distal firing shaft includes a pair of opposed proximal tabs that form a second hinge of the distal universal joint. The first and second hinges are interconnected by a distal bearing assembly. In certain embodiments, the distal bearing assembly includes a plurality of outer arcuate surfaces. Each outer arcuate surface is disposed in an inner arcuate surface defined in each of the pair of opposed distal tabs of the central tube and the pair of opposed proximal tabs of the distal firing shaft. In some embodiments, the gimbal defines a gimbal bore therethrough that is configured and adapted to receive the distal universal joint such that the gimbal is disposed around the distal universal joint.

In embodiments, a distal end portion of the proximal firing shaft defines a bore therein, the central tube defines a bore therethrough, and a proximal end portion of the distal firing shaft defines a bore therein. A spring wire is disposed within the bores of the proximal firing shaft, the central tube, and the distal firing shaft. In some embodiments, the spring wire is configured to bias the firing assembly along the longitudinal axis of the outer tube and is bendable upon articulation of the gimbal.

In some embodiments, the gimbal defines at least one slot in an outer surface thereof, and the at least one cable is secured within the at least one slot. In some embodiments, the outer tube includes a distal mounting member disposed therein that includes an outer surface that defines at least one recess, with the at least one cable extending through the recess.

In embodiments, the plurality of threaded sleeves is supported on at least one threaded screw. In some embodiments, the at least one threaded screw includes a first set of threads and a second set of threads. The first and second set of threads can be threaded in opposite directions. A first one of the plurality of threaded sleeves can be threadably engaged with the first set of threads and a second one of the plurality of threaded sleeves can be threadably engaged with the second set of threads. Rotation of the at least one threaded screw in a first rotational direction can approximate the first one and the second one of the plurality of threaded sleeves. Rotation of the at least one threaded screw in a second rotational direction can separate the first one and the second one of the plurality of threaded sleeves.

The adapter assembly may include an articulation actuator secured to the housing. In embodiments, the articulation actuator includes a joystick extending outwardly from the housing. The joystick is configured to move in a direction corresponding to a direction of articulation of the surgical loading unit. In some embodiments, the articulation actuator includes a plurality of directional switches disposed within the housing and the joystick includes a rocker configured and dimensioned to contact one or more of the directional switches upon movement of the joystick.

According to another aspect of the present disclosure, an electromechanical system includes a surgical loading unit including at least one axially translatable drive member, a handheld electromechanical surgical device including a housing and at least one rotatable drive shaft supported in the housing, and an adapter assembly selectively connectable between the housing of the surgical device and the surgical loading unit. The adapter assembly includes an articulation assembly and a firing assembly. The articulation assembly includes a gimbal and a plurality of threaded sleeves coupled to the gimbal by at least one cable. The plurality of threaded sleeves are movable to articulate the gimbal with the at least one cable. Articulation of the gimbal articulates the surgical loading unit. The firing assembly includes a firing shaft connectable between the at least one rotatable drive shaft of the surgical device and the at least one axially translatable drive member. The firing shaft includes at least one universal joint and is movable at the at least one universal joint with the gimbal to articulate the surgical loading unit and rotatable to translate the at least one axially translatable drive member through the surgical loading unit.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1A is a perspective view of an electromechanical surgical system in accordance with the principles of the present disclosure;

FIG. 1B is an enlarged, perspective view of the indicated area of detail shown in FIG. 1A;

FIG. 2 is an enlarged, perspective view of an adapter assembly of the electromechanical surgical system of FIG. 1A;

FIG. 3 is an enlarged, perspective view of a distal end portion of the adapter assembly shown in the indicated area of detail of FIG. 2;

DETAILED DESCRIPTION

Figure 4:
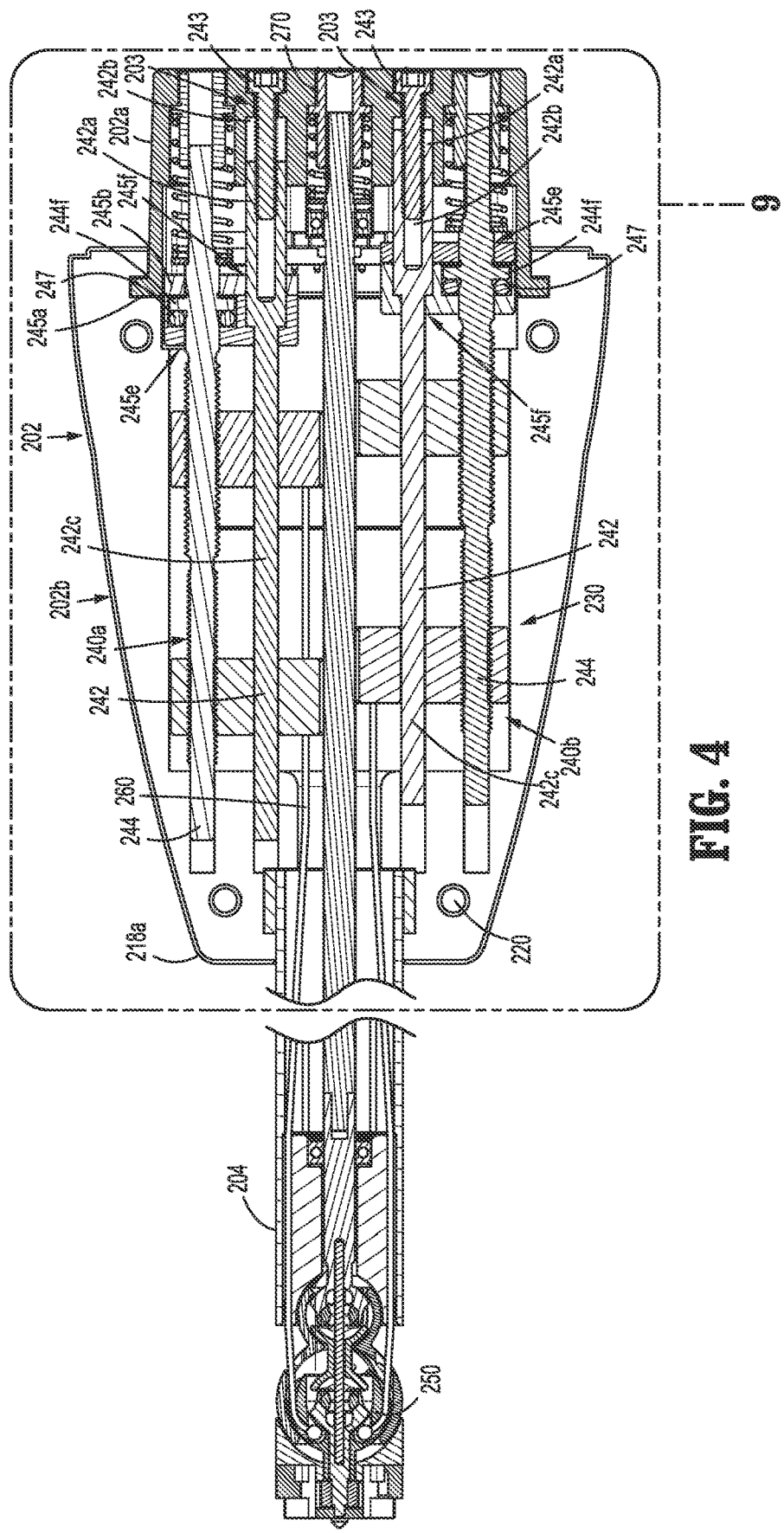
FIG. 4 is a bottom, cross-sectional view of the adapter assembly of FIG. 2, as taken along line 4-4 of FIG. 2, illustrating an articulation assembly thereof in a first condition.

Electromechanical surgical systems of the present disclosure include surgical devices in the form of powered handheld electromechanical instruments configured for selective attachment to a plurality of different end effectors that are each configured for actuation and manipulation by the powered handheld electromechanical surgical instrument. In particular, the presently described electromechanical surgical systems include adapter assemblies that interconnect the powered handheld electromechanical surgical instruments to the plurality of different end effectors. Each adapter assembly includes an articulation assembly and a firing assembly that is operatively coupled to a powered handheld electromechanical surgical instrument for effectuating actuation and/or manipulation thereof. The articulation assembly includes one or more cables that interconnect a gimbal and two or more threaded sleeves. The firing assembly includes at least one universal joint operatively connected with the gimbal. The gimbal couples to one of the plurality of end effectors such that axial movement of the threaded sleeves moves the one or more cables to rotate the gimbal and to bend the firing assembly in response to rotation of the gimbal to effectuate articulation of the end effector about a distal end of the adapter assembly.

Embodiments of the presently disclosed electromechanical surgical systems, surgical devices/handle assemblies, adapter assemblies, and/or loading units are described in detail with reference to the drawings, in which like reference numerals designate identical or corresponding elements in each of the several views. As used herein the term "distal" refers to that portion of the system, assembly, device, and/or component thereof, farther from the user, while the term "proximal" refers to that portion of the system, assembly, device, and/or component thereof, closer to the user.

Turning now to FIGS. 1A and 1B, an electromechanical surgical system, in accordance with the present disclosure, generally referred to as 10, includes a surgical device 100 in the form of a powered handheld electromechanical instrument, an adapter assembly 200, and a loading unit 300 (e.g., an end effector, multiple- or single-use loading unit). Surgical device 100 is configured for selective connection with adapter assembly 200, and, in turn, adapter assembly 200 is configured for selective connection with loading unit 300. Together, surgical device 100 and adapter assembly 200 may cooperate to actuate loading unit 300.

Surgical device 100 includes a handle housing 102 including a circuit board (not shown) and a drive mechanism (not shown) situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100. Handle housing 102 supports a plurality of motors (not shown), each in electrical communication with the circuit board and each including a rotatable drive shaft extending therefrom.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that is connected to or supporting adapter assembly 200 and/or loading unit 300.

Handle housing 102 provides a housing in which the drive mechanism (not shown) is situated. The drive mechanism is configured to drive shafts and/or gear components in order to perform the various operations of surgical device 100. In particular, the drive mechanism is configured to drive shafts and/or gear components in order to selectively articulate loading unit 300 about a longitudinal axis "X" and relative to a distal end of adapter assembly 200, to selectively rotate loading unit 300 about longitudinal axis "X" and relative to handle housing 102, to selectively move/approximate/separate an anvil assembly 310 and a cartridge assembly 320 of loading unit 300 relative to one another, and/or to fire a stapling and cutting cartridge within cartridge assembly 320 of loading unit 300.

Handle housing 102 defines a connection portion 104 configured to accept a proximal end of adapter assembly 200. Connection portion 104 houses an articulation contact surface 105 in electrical communication with the circuit board (not shown) and a plurality of rotatable drive shafts or connectors 106. Each rotatable drive shaft of the plurality of rotatable drive shafts 106 can be independently, and/or dependently, actuatable and rotatable by the drive mechanism or motors (not shown) housed within housing handle 102. In embodiments, the plurality of rotatable drive shafts 106 includes rotatable drive shafts, 106a, 106b, and 106c arranged in a common plane or line with one another. As can be appreciated, the plurality of rotatable drive shafts can be arranged in any suitable configuration. The drive mechanism (not shown) may be configured to selectively drive one of the rotatable drive shafts 106 of surgical instrument 100, at a given time.

Handle housing 102 supports a plurality of finger-actuated control buttons, rocker devices, and the like for activating various functions of surgical device 100. For example, handle housing 102 supports a plurality of actuators including, for example, an actuation pad 108 in operative registration with a plurality of sensors 108a that cooperate with actuation pad 108 to effectuate, for example, opening, closing, and/or firing of loading unit 300. Handle housing 102 can support actuators 107a, 107b which can be disposed in electrical communication with the motors of handle housing 102 to effectuate rotation of rotatable drive shafts 106a, 106b, and/or 106c for actuation thereof to enable adjustment of one or more of the components of adapter assembly 200. Any of the presently described actuators can have any suitable configuration (e.g., button, knob, toggle, slide, etc.)

Reference may be made to International Application No. PCT/US2008/077249, filed Sep. 22, 2008 (Inter. Pub. No. WO 2009/039506), and U.S. Patent Application Publication No. 2011/0121049, filed on Nov. 20, 2009 (U.S. Pat. No. 10,588,629), the entire contents of each of which being incorporated herein by reference, for a detailed description of various internal components of and operation of exemplary electromechanical surgical systems, the components of which are combinable and/or interchangeable with one or more components of electromechanical surgical systems 10 described herein.

With reference to FIGS. 2-3, adapter assembly 200 includes a housing 202 at a proximal end portion thereof and an outer tube 204 that extends distally from housing 202 to a distal end portion 204d thereof.

Turning now to FIGS. 4-9, housing 202 of adapter assembly 200 includes a proximal housing 202a and a distal housing 202b that support an articulation actuator 205 (FIGS. 5A-5B) to effectuate articulation of loading unit 300. As shown in FIGS. 5A-5B, articulation actuator 205 includes a support member 205a disposed within proximal housing 202a and including a plurality of directional switches 205b disposed thereon in electrical communication with articulation contact surface 105 (FIG. 1A) of surgical device 100. Alternatively, directional switches 205b are in operative communication (e.g., wireless communication) with the circuit board (not shown) of surgical device 100. A joystick 205c is pivotally coupled to support member 205a and includes a knob 205d and a rocker 205e disposed at opposed ends thereof. Knob 205d extends outwardly from the proximal housing 202a and is configured for actuation by a finger of a user. Rocker 205e is configured and dimensioned to contact one or more of directional switches 205b when joystick 205c is pivoted/deflected in a corresponding direction by actuation of knob 205d to enable omni-directional articulation of loading unit 300 relative to adapter assembly 200. Joystick 205c is biased in a centered position such that rocker 205e does not contact any of directional switches 205b. In embodiments, directional switches 205b correspond to different yaw and/or pitch angles, relative to longitudinal axis "X," to which loading unit 300 can be moved, upon activation of one or more of the directional switches 205b in response to a deflection direction and/or angle of joystick 205c.

Figure 5A:
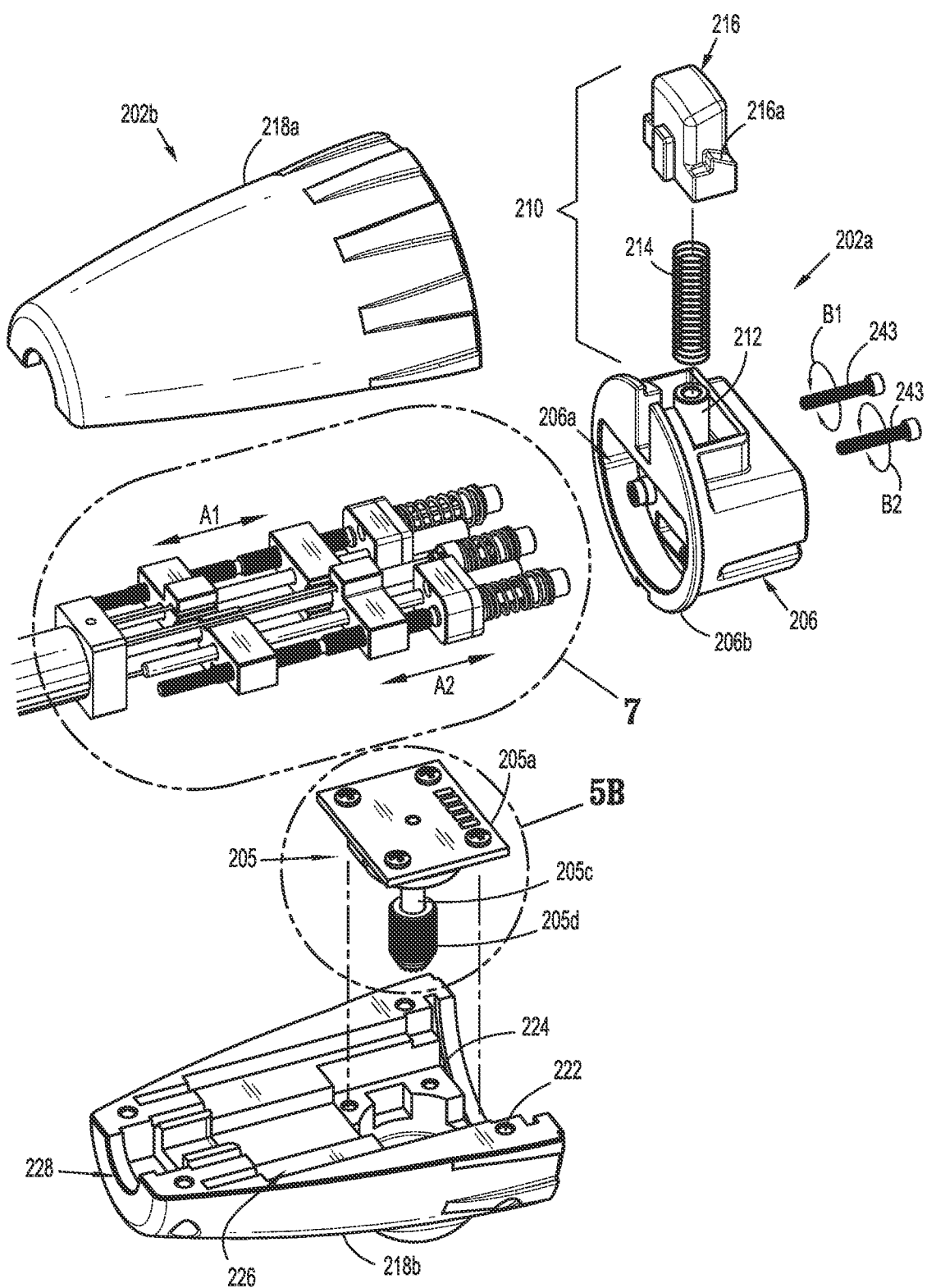
FIG. 5A is a side, perspective view, with parts separated, of a proximal portion of the adapter assembly of FIG. 2.
Figure 5B:
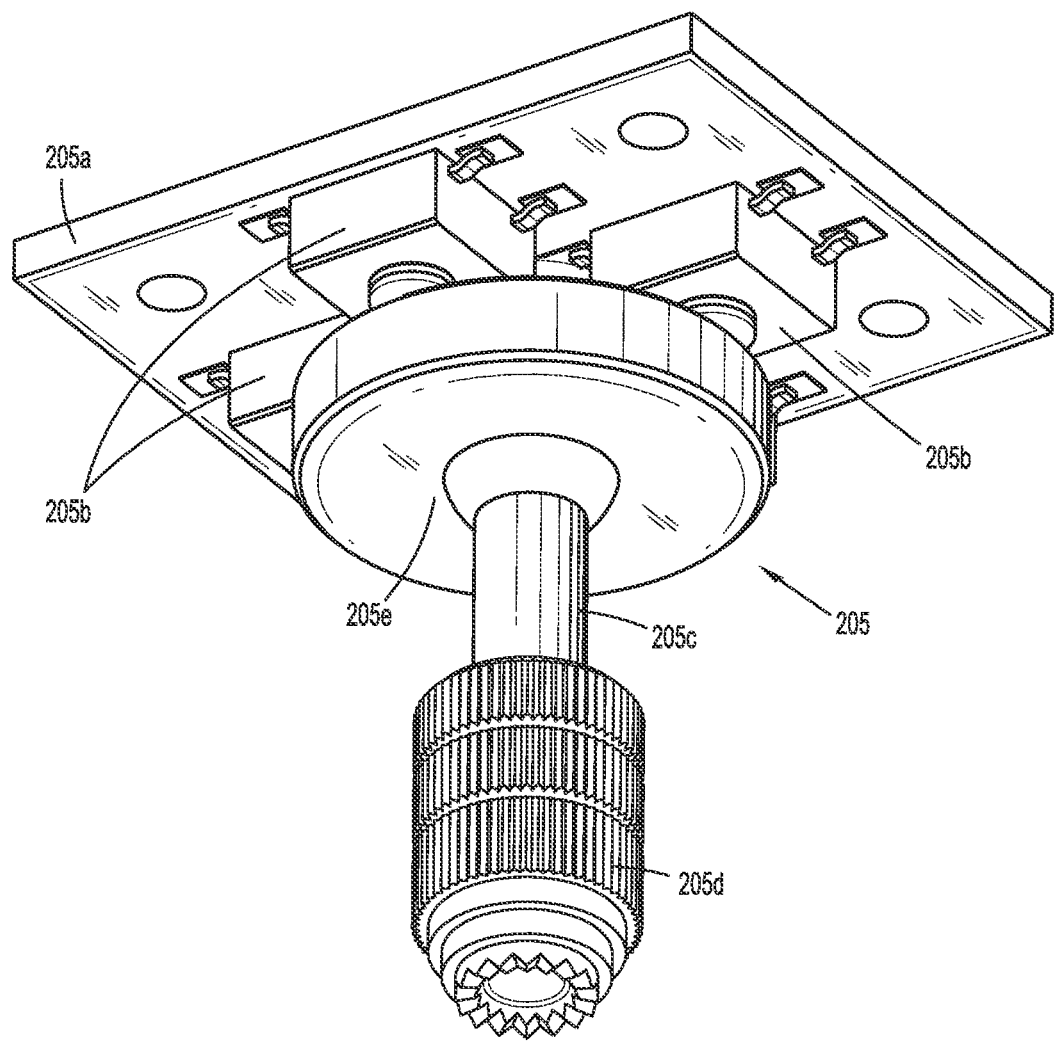
FIG. 5B is an enlarged perspective view of an actuator of the proximal portion of the adapter assembly of FIG. 5A.

With continued reference to FIG. 5A, proximal housing 202a includes a housing body 206 defining a central slot 206a therethrough and having a distal lip 206b extending radially outwardly therefrom. Housing body 206 supports a mounting assembly 210 thereon. Mounting assembly 210 is supported on housing body 206 and includes a shaft 212 that extends outwardly from housing body 206, a spring 214 that is supported about an outer surface of shaft 212, and a mounting button 216 that engages spring 214 and shaft 212. Spring 214 contacts a bottom surface of mounting button 216 to bias mounting button 216 upwardly to an extended position spaced from housing body 206. Spring 214 is sufficiently compressible to enable mounting button 216 to be depressed downwardly from the extended position to a compressed position. In the compressed position, mounting button 216 is disposed in close approximation with housing body 206 and offset from the extended position. Mounting button 216 includes sloped engagement features 216a that are configured to contact connection portion 104 (FIG. 1A) of handle housing 102 while mounting button 216 is in the extended position to facilitate securement of housing 202 to connection portion 104 of handle housing 102.

As seen in FIGS. 4 and 5A, distal housing 202b includes a first half-section 218a and a second half-section 218b. First half-section 218a includes a plurality of pins 220 extending therefrom and second half-section 218b defines a plurality of bores 222 adapted to receive the plurality of pins 220 of first half-section 218a to mate the first and second half-sections 218a, 218b together. Each of first and second half-sections 218a, 218b defines an internal lip receiving annular recess 224 adapted to receive a portion of distal lip 206b of proximal housing 202a to facilitate securement of proximal and distal housings 202a, 202b. Each of first and second half-sections 218a, 218b defines an articulation-assembly-receiving recess 226 that is in communication with an outer-tube-receiving channel 228. Each outer-tube-receiving channel 228 is defined through a distal end of one of first and second half-sections 218a, 218b.

Figure 6:
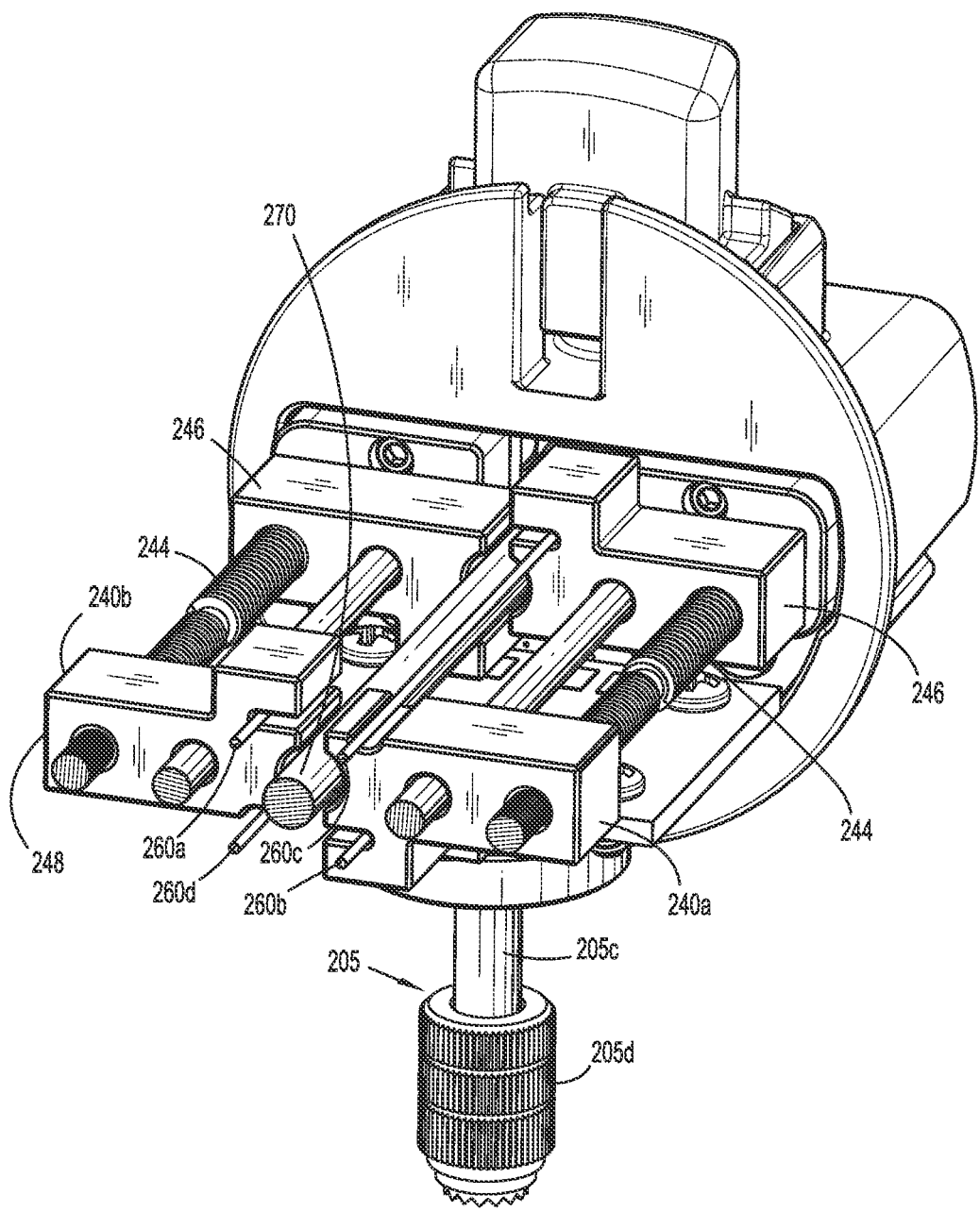
FIG. 6 is front, perspective view of the proximal portion of the adapter assembly of FIG. 2, as taken along line 6-6 of FIG. 4.

An articulation assembly 230 is supported within housing 202 and outer tube 204. Articulation assembly 230 includes a pair of sleeve assemblies 240a, 240b at a proximal end thereof and a gimbal 250 at a distal end thereof. The pair of sleeve assemblies 240a, 240b and the gimbal 250 are connected by a plurality of cables 260. As depicted in FIG. 6, and described in greater detail below, the plurality of cables 260 includes a first cable 260a, a second cable 260b, a third cable 260c, and a fourth cable 260d.

With reference to FIGS. 6-9, in conjunction with FIGS. 4 and 5A, each of the pair of sleeve assemblies 240a, 240b includes a support shaft 242, a threaded screw assembly 244, a bearing block 245, and a pair of threaded sleeves 246, 248.

As seen in FIG. 4, support shaft 242 includes a proximal portion 242a received in central slot 206a (see FIG. 5A) of proximal housing 202a. Proximal portion 242a of support shaft 242 defines a threaded bore 242b therein. Each threaded bore 242b receives therein a screw 243 that is advanced through a screw passage 203 defined in proximal housing 202a to facilitate securement of articulation assembly 230 to proximal housing 202a. Support shaft 242 further includes a distal portion 242c that extends distally from proximal portion 242a.

With reference to FIG. 5A, each screw 243 can function as a cable tensioner to adjust overall slack and/or tension in one or more of the plurality of cables 260 as depicted by axial lines of translation "A1" and "A2" of the pair of sleeve assemblies 240a, 240b and by rotational arrows "B1" and "B2" of screws 243. For example, with reference again to FIG. 4, the pair of sleeve assemblies 240a, 240b are disposed in offset longitudinal relationship with respect to each other (e.g., compare relative longitudinal relationship between bearing blocks 245 and/or distal ends of threaded screw assemblies 244) to depict differences in slack adjustment in each sleeve assembly 240*a*, 240*b*. In embodiments, slack or tension adjustments of one of the pair of sleeve assemblies 240*a*, 240*b* can be different and/or the same as the other of the pair of sleeve assemblies 240*a*, 240*b*, and likewise can be further adjusted as necessary to achieve a desired cable slack or tension in one or more of the plurality of cables 260. In particular, clockwise and/or counterclockwise (e.g., tightening and/or loosening) rotation of screw 243 relative to one of threaded bores 242*b* approximates and/or separates screw 243 relative to support shaft 242 to axially move one or both of the pair of sleeve assemblies 240*a*, 240*b* (proximally and/or distally) to adjust slack or tension in one or more of the plurality of cables 260. In embodiments, rotation of one or both screws 243 in a first direction, draws one or both of the pair of sleeve assemblies 240*a*, 240*b* proximally, and rotation of one or both screws in a second direction, distally advances one or both of the pair of sleeve assemblies 240*a*, 240*b*. In some embodiments, rotation in the first direction of one or both screws 243 draws one or both of the pair of sleeve assemblies 240*a*, 240*b* proximally, and rotation in the second direction of one or both screws 243 distally advances one or both of the pair of sleeve assemblies 240*a*, 240*b*. As can be appreciated, each screw 243 can be independently and/or dependently rotatable with respect to the other screw 243.

Threaded screw assembly 244 includes a threaded screw 244*a* extending distally from an input socket 244*b* with a distal end of input socket 244*b* being mechanically coupled to a proximal end of threaded screw 244*a*. Each input socket 244*b* is configured to engage one of the plurality of rotatable drive shafts 106 of handle housing 102. For example, input socket 244*b* of sleeve assembly 240*b* can be mechanically coupled to rotatable drive shaft 106*a* and input socket 244*b* of sleeve assembly 240*a* can be mechanically coupled to rotatable drive shaft 106*c*.

Threaded screw 244*a* includes a first thread portion 244*c* and a second thread portion 244*d* that are threaded in opposite directions to one another. For example, first thread portion 244*c* can be a left-hand thread and second thread portion 244*d* can be a right-hand thread, or vice-versa. In embodiments, first and second thread portions 244*c*, 244*d* have the same thread pitch. Threaded screw 244*a* can include a third thread portion 244*e*. Third thread portion 244*e* can be either right or left handed and can have the same and/or different pitch as the first and/or second thread portions 244*c*, 244*d*. As can be appreciated, any of first, second, or third thread portions 244*c*, 244*d*, 244*e* can have any suitable pitch, shape, dimension, and/or configuration. With reference to FIG. 4, threaded screw 244 includes a retaining member or flange 244*f* extending from an outer surface thereof.

Figure 8:
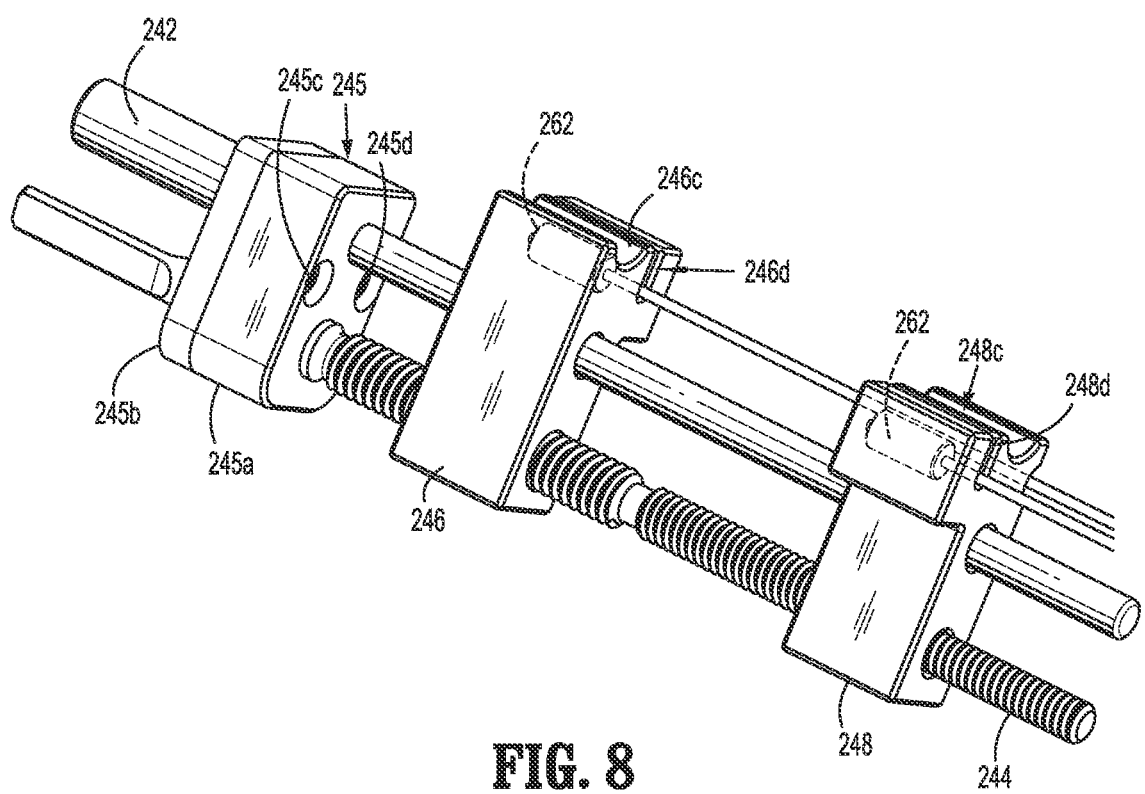
FIG. 8 is an enlarged, bottom perspective view of a section of the portion of the articulation assembly shown in FIG. 7.

As seen in FIG. 8, bearing block 245 is mounted on proximal end portion of support shaft 242 and on threaded screw assembly 244. Bearing block 245 includes distal plate 245*a* and a proximal plate 245*b* that are secured together by a pair of fasteners 245*c*, 245*d*. With reference also to FIG. 4, distal and proximal plates 245*a*, 245*b* define first and second channels 245*e*, 245*f* therethrough. First channel 245*e* receives a proximal portion of threaded screw 244 and encloses retaining member 244*f* and a thrust bearing 247. Second channel 245*f* receives support shaft 242, which can be fixedly secured therein to facilitate axial advancement of one of the pair of sleeve assemblies 240*a*, 240*b* upon rotation of screws 243 as described above. As can be appreciated, bearing block 245 of sleeve assembly 240*a* is a mirror image of bearing block 245 of sleeve assembly 240*b*.

Figure 7:
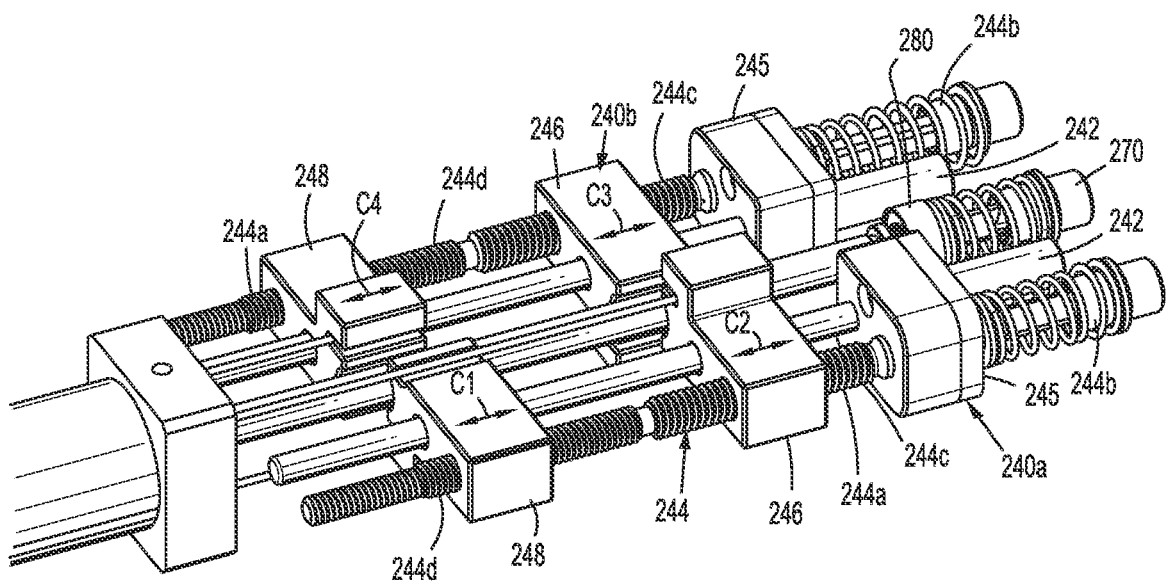
FIG. 7 is an enlarged, side perspective view of a portion of the articulation assembly and a portion of a firing assembly, with the articulation assembly shown in the first condition.
Figure 9:
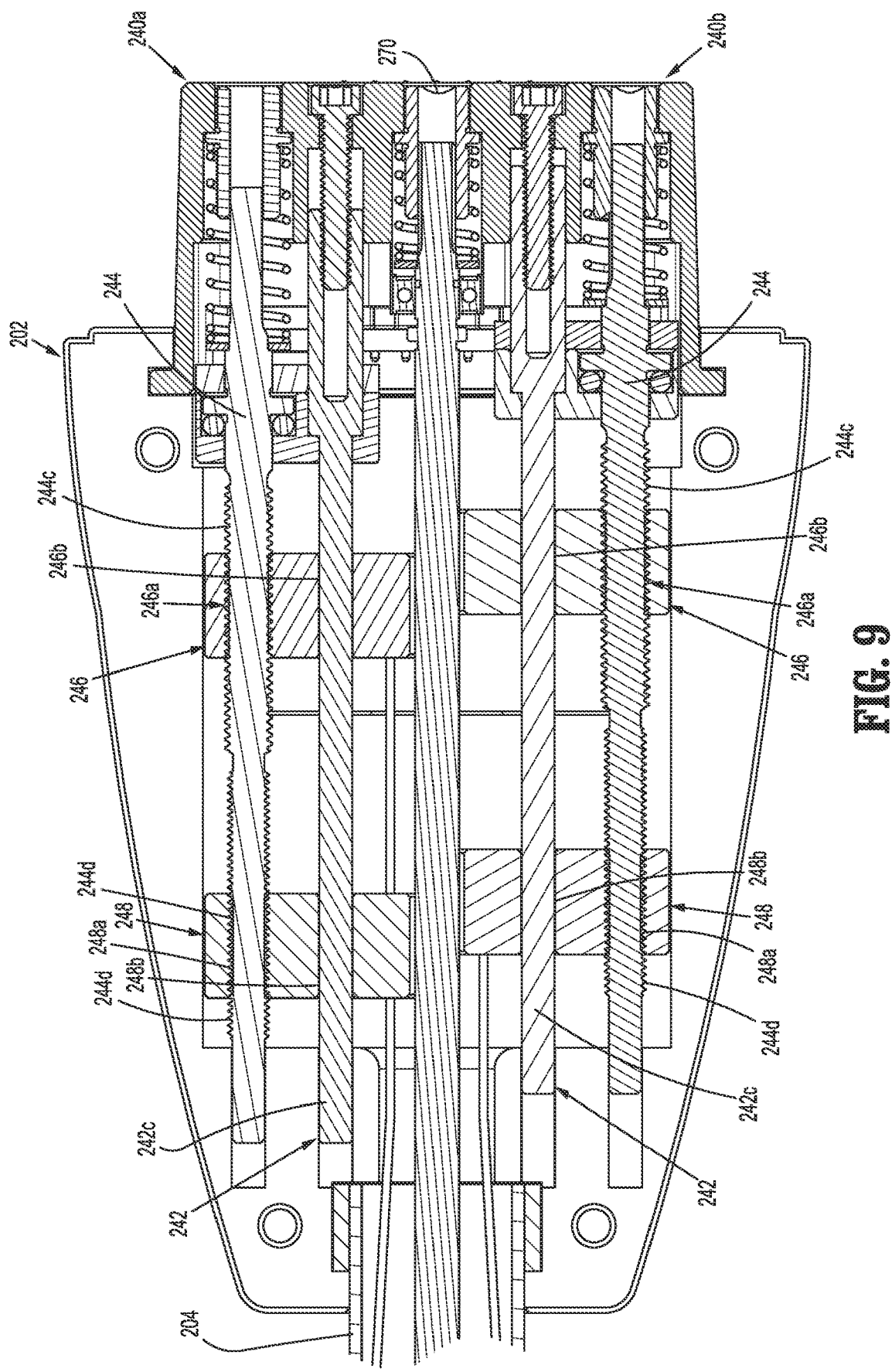
FIG. 9 is an enlarged, cross-sectional, bottom view of the indicated area of detail shown in FIG. 4, with the articulation assembly being shown in a second condition.

Referring to FIGS. 7 and 8, each of the pair of threaded sleeves 246, 248 has an L-shaped profile. As seen in FIG. 9, threaded sleeve 246 defines first and second bores 246*a*, 246*b* therethrough with first bore 246*a* being threaded and second bore 246*b* being smooth. Similarly, threaded sleeve 248 defines first and second bores 248*a*, 248*b* therethrough with first bore 248*a* being threaded and second bore 248*b* being smooth. Each of the pair of sleeve assemblies 240*a*, 240*b* is arranged so that threaded bores 246*a*, 248*a* receive a threaded screw 244*a* such that first thread portion 244*c* threadably engages threaded bore 246*a* and such that second thread portion 244*d* threadably engages threaded bore 248*a*. Each of the pair of sleeve assemblies 240*a*, 240*b* is also arranged so that smooth bores 246*b*, 248*b* of threaded sleeves 246, 248 receive distal portion 242*c* of support shaft 242 such that threaded sleeves 246, 248 move axially along distal portion 242*c* of support shaft 242. In embodiments, threaded sleeve 246 of sleeve assembly 240*a* can be disposed in mirrored relation with threaded sleeve 246 of sleeve assembly 240*b*.

As seen in FIG. 8, each of the pair of threaded sleeves 246, 248 define shaft-receiving channels 246*c*, 248*c* and cable-receiving channels 246*d*, 248*d* in side surfaces thereof. Each of the pair of threaded sleeves 246, 248 is coupled to one of the plurality of cables 260 by a cable ferrule 262 connected to a proximal end of each of the plurality of cables 260. Cable-receiving channels 246*d*, 248*d* receive cable ferrule 262 of one of the plurality of cables 260 therein to secure one of the plurality of cables 260 to each of the pair of threaded sleeves 246, 248.

With reference to FIGS. 10A-13, each of the plurality of cables 260 extends distally to a retaining ball 262 (see FIG. 13) to secure the distal end of the first, second, third, and fourth cables 260*a*-260*d* to gimbal 250. Each opposite pair of the plurality of cables 260 can have two cables that are secured to gimbal 250 at locations 180 degrees apart (e.g., first and fourth cables 260*a*, 260*d* or second and third cables 260*b*, 260*c*).

As seen in FIG. 6, each opposite pair of the plurality of cables 260 has proximal ends that connect to the pair of threaded sleeves 246, 248 on the same threaded screw 244. Thus, the proximal end of the first and fourth cables 260*a*, 260*d* connect to one threaded screw 244, and the proximal end of the second and third cables 260*b*, 260*c* connect to the other threaded screw 244. It is contemplated that one or more of the plurality of cables can criss-cross within outer tube 204.

Referring again to FIGS. 10A-13, gimbal 250 has a proximal portion 250*a* with a generally rounded shape and a distal portion 250*b* extending from proximal portion 250*a*. Proximal portion 250*a* defines a plurality of ball-retaining slots 252 (e.g., four) in a distal outer surface thereof so that each ball-retaining slot of the plurality of ball-retaining slots 252 is dimensioned to receive one of retaining balls 262 of the plurality of cables 260 to secure each of the plurality of cables 260 to gimbal 250.

Proximal portion 250*a* of gimbal 250 includes a plurality of spaced apart wings 254 that extend from an outer surface thereof. Each wing of the plurality of spaced-apart wings 254 includes a top surface 254*a* and side surfaces 254*b*. Side surfaces 254*b* of adjacent wings of the plurality of spaced-apart wings 254 define a plurality of slots 256 about the outer surface of proximal portion 250*a*. The plurality of slots 256, which are configured to receive the plurality of cables 260, are in communication with the plurality of ball-retaining slots 252 and extend proximally therefrom.

Distal portion 250b of gimbal 250 includes a tubular shaft 251 having a flange 253 extending outwardly from an outer surface of tubular shaft 251. Proximal and distal portions 250a, 250b of gimbal 250 define a gimbal bore 258 (see FIGS. 11-12) that extends therethrough and includes first section 258a defined by inner surfaces of distal portion 250b and a second section 258b defined by inner surfaces of proximal portion 250a.

Figure 14:
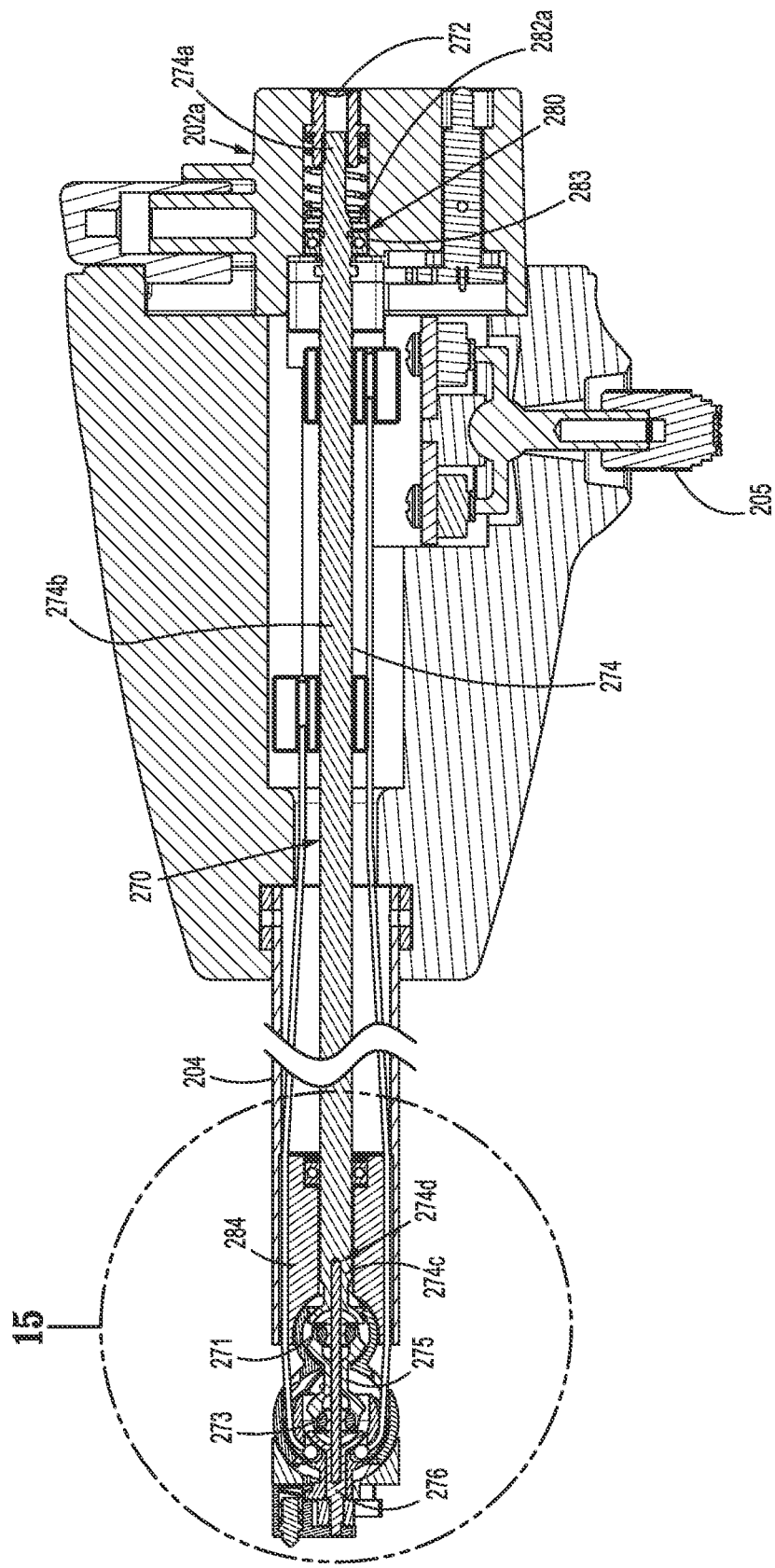
FIG. 14 is a side, cross-sectional view of the adapter assembly of FIG. 2, as taken along line 14-14 of FIG. 2.

Referring to FIG. 14, a firing assembly 270 is supported within housing 202 and outer tube 204 of adapter assembly 200. Firing assembly 270 includes an input socket 272 adapted to couple to rotatable drive shaft 106b of housing handle 102 (see FIG. 1A), a proximal firing shaft 274 extending distally from input socket 272, a central tube 275 extending distally from the proximal firing shaft 274, and a distal firing shaft 276 extending distally from central tube 275. Proximal firing shaft 274 and central tube 275 intersect at proximal universal joint 271, and central tube 275 and distal firing shaft 276 intersect at distal universal joint 273.

With continued reference to FIG. 14, a housing bearing member 280 supports a proximal end of proximal firing shaft 274 within proximal housing 202a, and proximal and distal mounting members 282, 284 support a distal end of proximal firing shaft 274 within outer tube 204. Housing bearing member 280 includes a thrust bearing 283 that receives proximal firing shaft 274 therethrough to enable proximal firing shaft 274 to rotate. Proximal mounting member 282 defines a central passage 282a therethrough that receives the proximal firing shaft 274.

Figure 10A:
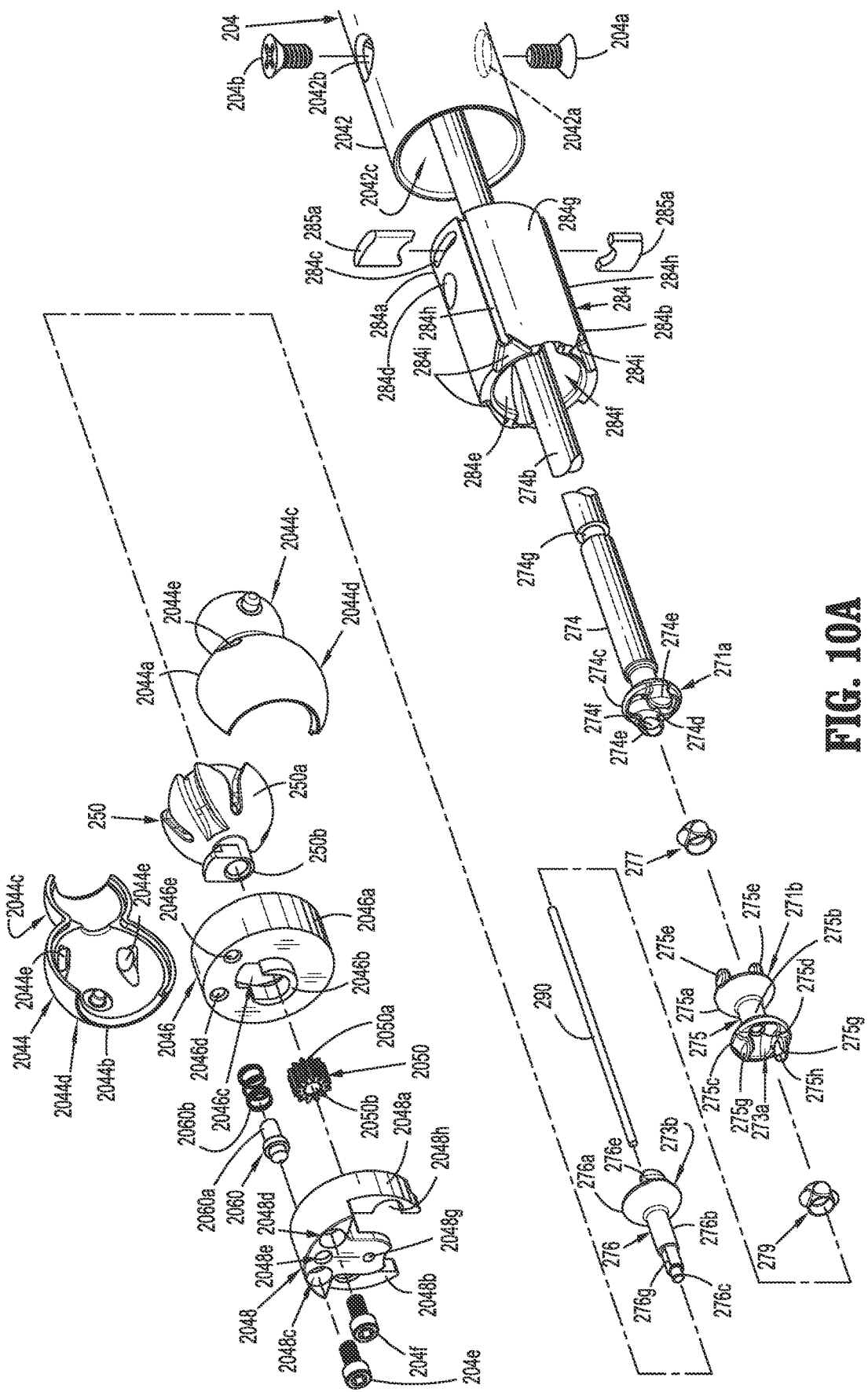
FIG. 10A is an enlarged, perspective view, with parts separated, of the distal portion of the adapter assembly shown in FIG. 3.
Figure 10B:
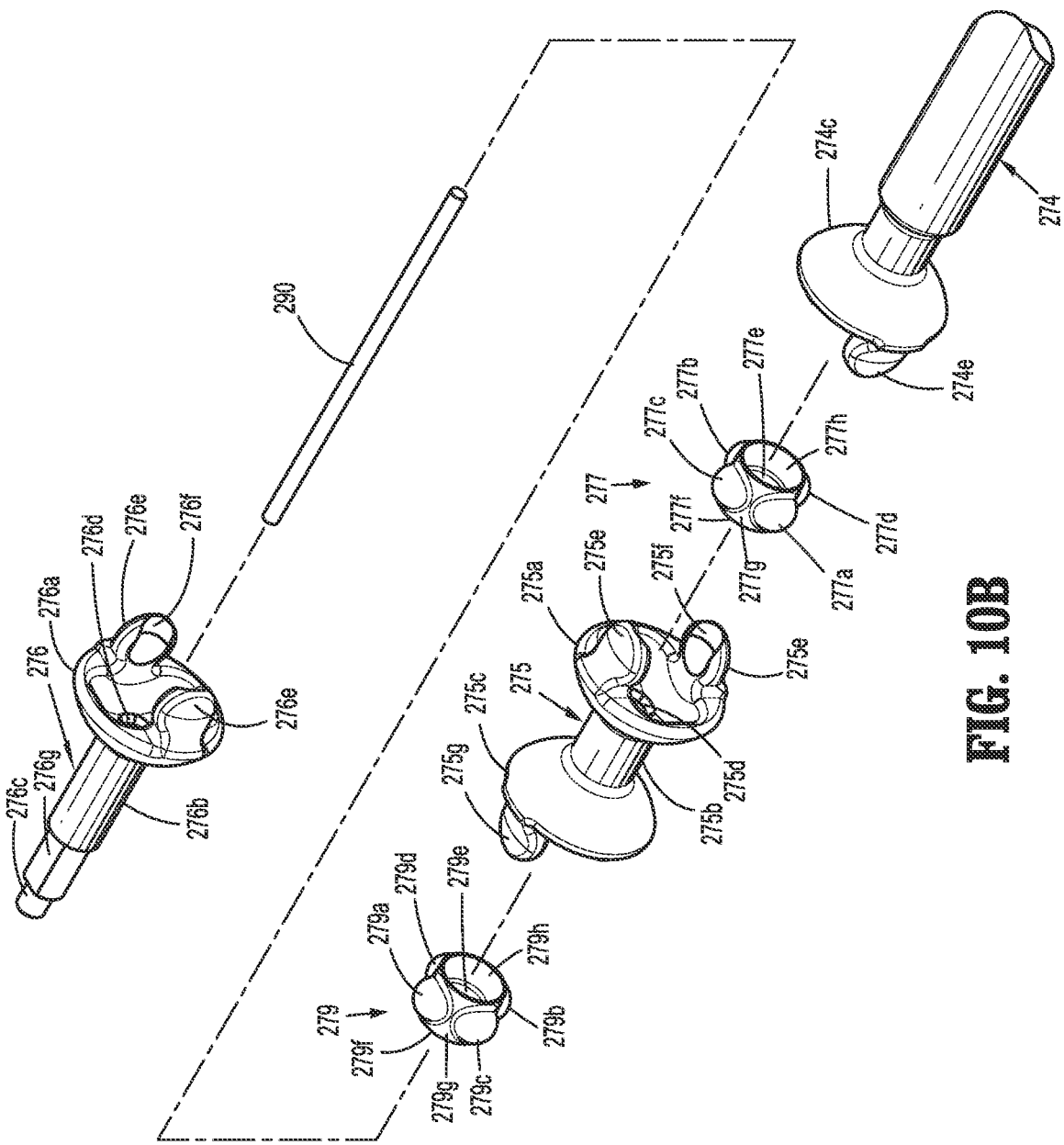
FIG. 10B is an enlarged, perspective view, with parts separated, of a firing assembly of the distal portion of the adapter assembly of FIG. 10A.
Figure 11:
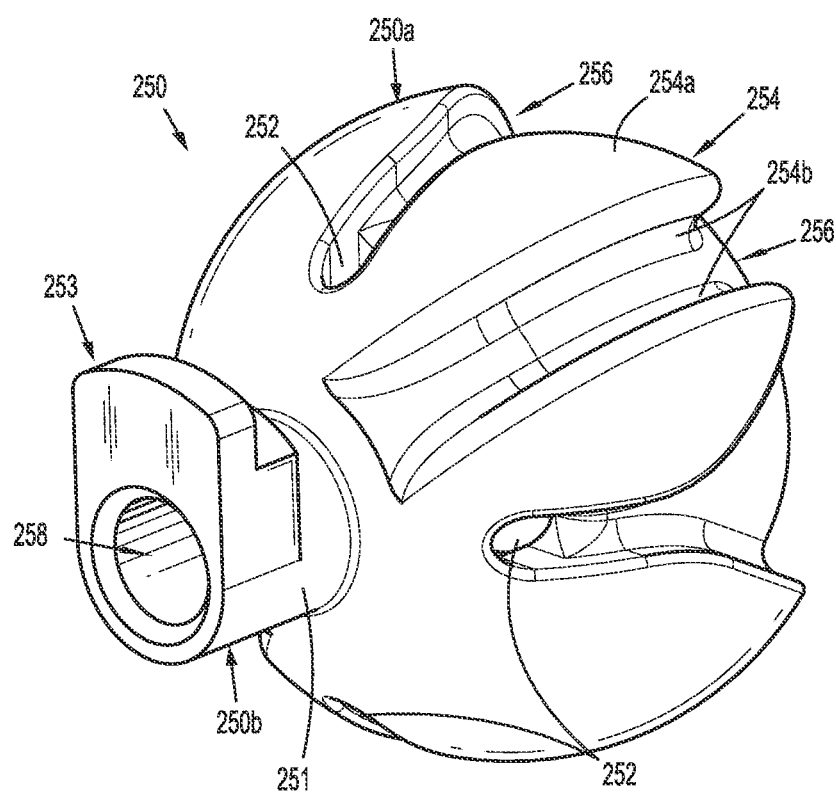
FIG. 11 is an enlarged, perspective view of a gimbal of the articulation assembly.
Figure 12:
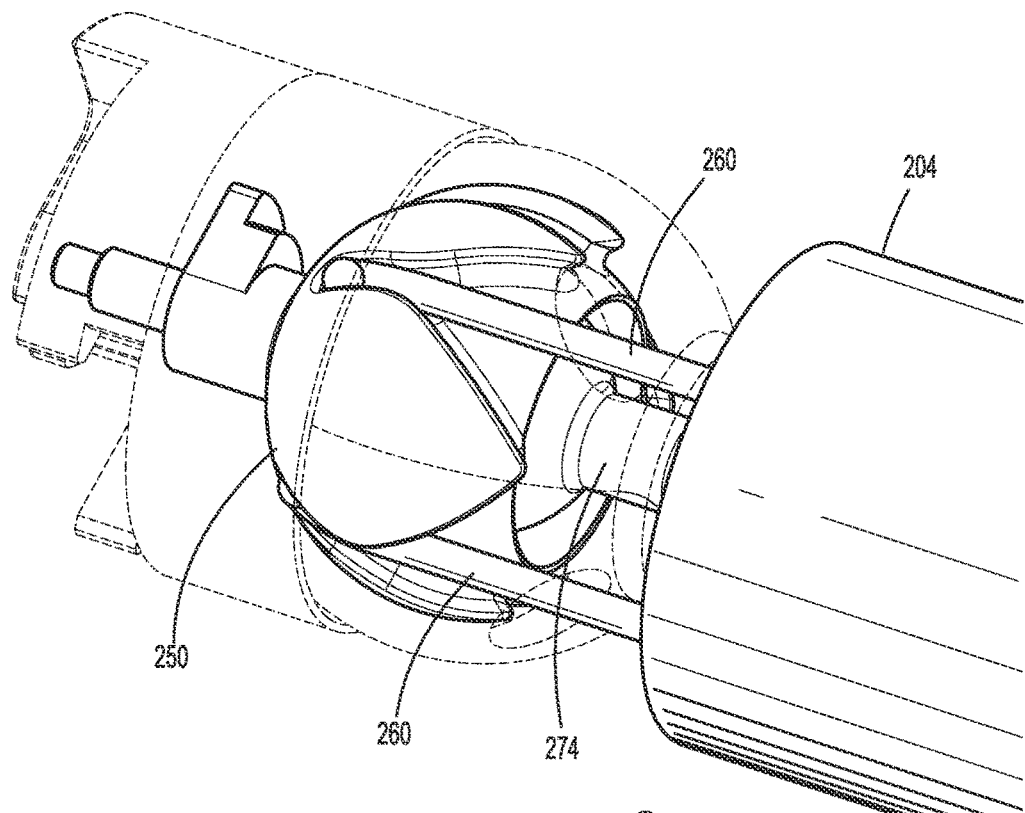
FIG. 12 is an enlarged, side, perspective view of the distal portion of the adapter assembly shown in FIG. 3, with portions thereof removed for clarity, the distal portion of the adapter assembly being shown in a non-articulated condition.
Figure 13:
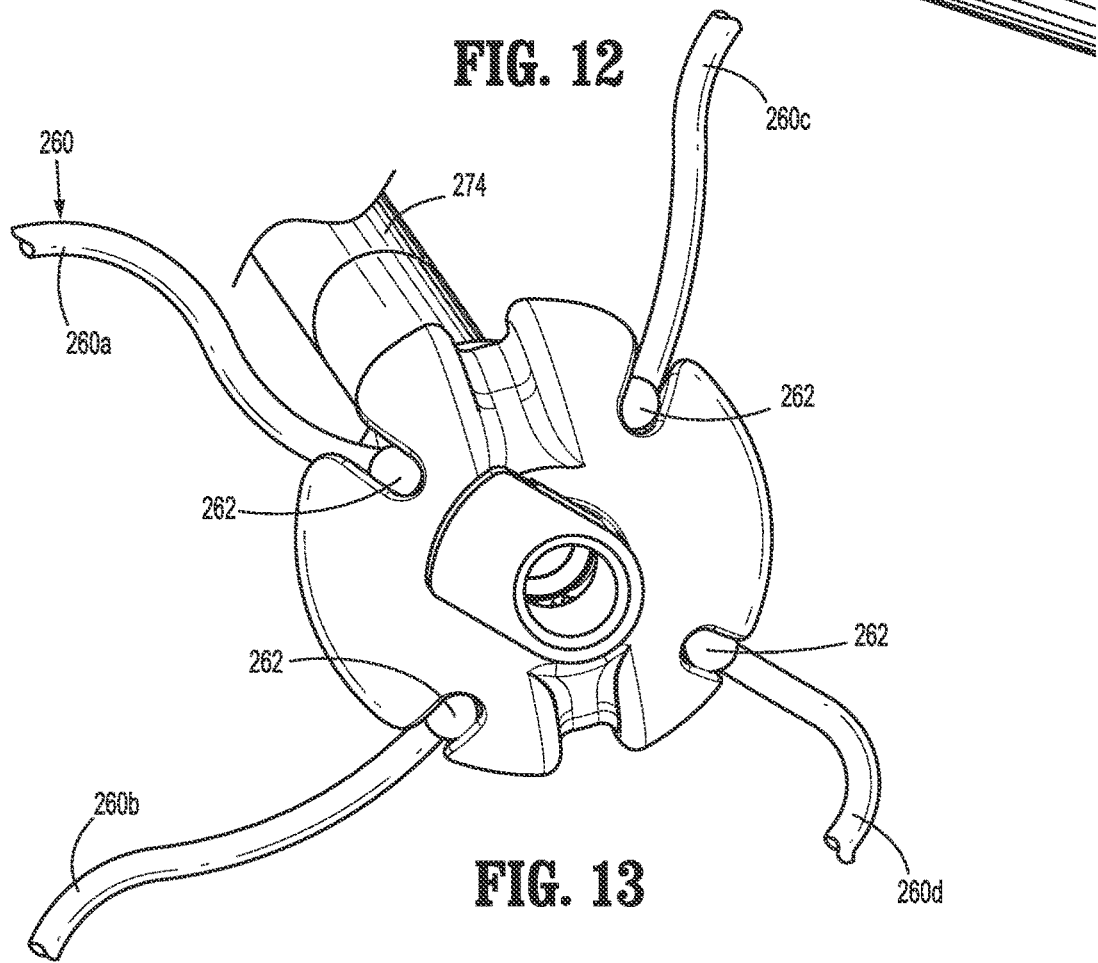
FIG. 13 is an enlarged, front, perspective view of a distal portion of the articulation assembly.
Figure 15:
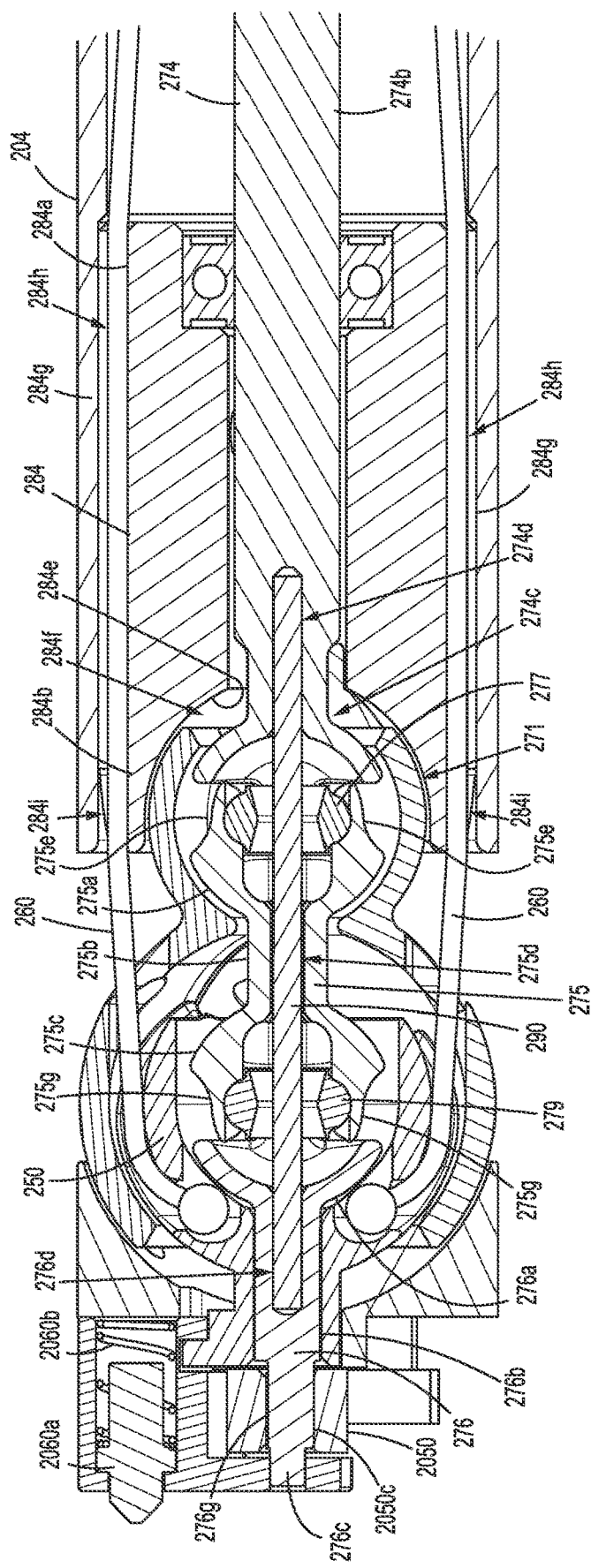
FIG. 15 is an enlarged, side, cross-sectional view of the indicated area of detail shown in FIG. 14.

As seen in FIGS. 10A, 14, and 15, distal mounting member 284 includes a proximal section 284a and a distal section 284b. Proximal section 284a defines a pair of slots 284c and a pair of screw openings 284d therethrough, with each of the pair of slots 284c and the pair of screw openings 284d disposed on opposed top and bottom surfaces. The pair of slots 284c receives a respective pair of pins 285a to secure distal mounting member 284 about a recess 274g defined in proximal firing shaft 274 to allow rotation of proximal firing shaft 274 relative to pins 285a. Distal section 284b of distal mounting member 284 includes an inner surface 284e that defines a hemispherical opening 284f that receives a proximal portion of proximal universal joint 271 to enable articulation of proximal universal joint 271 about at least two axes orthogonal to longitudinal axis "X" upon articulation of gimbal 250. Distal mounting member 284 includes an outer surface 284g that defines a plurality of recesses 284h (e.g., four), with each of the recesses 284h dimensioned to receive one of the plurality of cables 260 extending from between gimbal 250 and the pair of sleeve assemblies 240a, 240b. In embodiments, recesses 284h have a distal tapered portion 284i to enable cable 260 extending therethrough to move over an increased range of motion during articulation of gimbal 250.

With continued reference to FIGS. 10A, 10B, 14, and 15, proximal firing shaft 274 includes a proximal end portion 274a that is received in a distal end of input socket 272, a body portion 274b extending distally from proximal end portion 274a, and a distal end portion 274c having a hemispherical shape that extends distally from body portion 274b. Distal end portion 274c includes a bore 274d defined therein and a pair of opposed distal tabs 274e that form a first hinge 271a of proximal universal joint 271. Each of the distal tabs 274e has an inner arcuate surface 274f in which outer arcuate surfaces 277a, 277b of a proximal bearing assembly 277 are disposed. Outer arcuate surfaces 277a, 277b are complementary in shape with inner arcuate surfaces 274f In embodiments, inner arcuate surfaces 274f are concave surfaces and outer arcuate surfaces 277a, 277b are convex surfaces. Proximal bearing assembly 277 includes a ring-shaped body 277f including a plurality of outer arcuate surfaces 277a-277d extending from an outer surface 277g of ring-shaped body 277f. An inner surface 277h of ring-shaped body 277f defines an opening 277e therethrough.

Central tube 275 includes proximal and distal end portions 275a, 275c each having a hemispherical shape and a body portion 275b extending between proximal and distal end portions 275a, 275c. Central tube 275 defines a bore 275d extending longitudinally therethrough. Proximal end portion 275a of central tube 275 includes a pair of opposed proximal tabs 275e that form a second hinge 271b of proximal universal joint 271. The pair of opposed proximal tabs 275e are maintained at about a 90° angle with respect to the pair of opposed distal tabs 274e of proximal firing shaft 274. Each of the proximal tabs 275e has an inner arcuate surface 275f in which outer arcuate surfaces 277c, 277d of proximal bearing assembly 277 are disposed. First and second hinges 271a, 271b are pivotable about proximal bearing assembly 277 independent of each other about at least two orthogonal axes and are rotatable together about longitudinal axis "X." Distal end portion 275c of central tube 275 includes a pair of opposed distal tabs 275g that form a first hinge 273a of distal universal joint 273. Each of the distal tabs 275g of central tube 275 has an inner arcuate surface 275h in which outer arcuate surfaces 279a, 279b of a distal bearing assembly 279 are disposed. Similar to proximal bearing assembly 277, distal bearing assembly 279 includes a ring-shaped body 279f including a plurality of outer arcuate surfaces 279a-279d extending from an outer surface 279g of ring-shaped body 279f An inner surface 279h of ring-shaped body 279f defines an opening 279e therethrough.

Distal firing shaft 276 includes a proximal end portion 276a having a hemispherical shape, a body portion 276b extending distally from proximal end portion 276a and defining a ledge 276g that is recessed from an outer surface thereof, and a distal end portion 276c extending distally from body portion 276b. Proximal end portion 276a includes a bore 276d defined therein and a pair of opposed proximal tabs 276e that form a second hinge 273b of distal universal joint 273. The pair of opposed proximal tabs 276e of the distal firing shaft 276 are maintained at about a 90° angle with respect to the pair of opposed distal tabs 275g of central tube 275. Each of the proximal tabs 276e has an inner arcuate surface 276f in which outer arcuate surfaces 279c, 279d of distal bearing assembly 279 are disposed. Distal universal joint 273 is substantially the same as proximal universal joint 271 and is formed by first and second hinges 273a, 273b that are interconnected by distal bearing assembly 279 such that first and second hinges 273a, 273b are pivotable about distal bearing assembly 279 independently of each other and are rotatable together.

Bore 274d defined in distal end portion 274c of proximal firing member 274 cooperates with each of opening 277e defined in proximal bearing assembly 277, bore 275d defined through central tube 275, opening 279e defined in distal bearing assembly 279, and bore 276d defined in proximal end portion 276a of distal firing shaft 276 to receive a spring wire 290. Spring wire 290 is formed from resilient metals and/or polymers, such as nitinol, spring stainless steel, alloys thereof, and the like. Spring wire 290 is configured to bias the firing assembly 270 along longitudinal axis "X" and is bendable upon articulation of gimbal 250.

As seen in FIGS. 3, 10A, and 15, distal end portion 2040 of outer tube 204 includes a first segment 2042, a second segment 2044, a third segment 2046, and a fourth segment 2048.

First segment 2042 of distal end portion 2040 of outer tube 204 defines a pair of screw openings 2042a, 2042b that correspond with the pair of screw openings 284d of distal mounting member 284. The pair of screw openings 2042a, 2042b of first segment 2042 and the pair of screw openings 284d of distal mounting member 284 receive a pair of screws 204a, 204b to secure proximal section 284a of distal mounting member 284 within an opening 2042c defined within a distal end of first segment 2042.

Second segment 2044 of distal end portion 2040 of outer tube 204 includes first and second shell halves 2044a and 2044b that matingly engage each other, for example, by snap or friction fit, around proximal and distal universal joints 271, 273. A proximal section 2044c of second segment 2044 is secured within hemispherical opening 284f of distal mounting member 284 and is rotatable therein. A distal section 2044d of second segment 2044 is configured to receive distal portion 250b of gimbal 250 which is disposed around distal universal joint 273. Second segment 2044 further includes a plurality of openings 2044e configured to receive cables 260 extending from gimbal 250 proximally toward the pair of threaded sleeves 246, 248.

Third segment 2046 of distal end portion 2040 of outer tube 204 has a cylindrical body 2046a that mounts over proximal section 2044c of second segment 2044. Third segment 2046 includes a U-shaped shoe 2046b that extends distally from a distal surface of cylindrical body 2046a. A central channel 2046c is defined through U-shaped shoe 2046b and cylindrical body 2046a, and is configured to receive distal section 2044d of second segment 2044 which is rotatable therein.

Fourth segment 2048 of distal end portion 2040 of outer tube 204 includes a pair of arms 2048a, 2048b that extends from fourth segment 2048. The pair of arms 2048a, 2048b are disposed in spaced apart and mirrored relation to one another. A pair of screw openings 2048c, 2048d is defined in fourth segment 2048 and are aligned with a pair of screw bores 2046d, 2046e defined within third segment 2046 so that a pair of screws 204e, 204f can be received by the pair of screw openings 2048c, 2048d of the fourth segment 2048 and the pair of screw bores 2046d, 2046e of the third segment 2046 to secure third and fourth segments 2046, 2048 together. Fourth segment 2048 defines a plunger opening 2048e that receives a plunger assembly 2060 of distal end portion 2040 of outer tube 204.

Plunger assembly 2060 includes a plunger 2060a that is biased through plunger opening 2048e by a spring 2060b (see FIG. 15). Plunger assembly 2060 and the pair of arms 2048a, 2048b cooperate to facilitate securement of the proximal end of loading unit 300 to distal end portion 2040, as described in greater detail below (see FIGS. 17A and 17B).

As illustrated in FIG. 10A, a tongue 2048f depends from fourth segment 2048 and defines an opening 2048g therethrough that receives distal tip 276c of distal firing shaft 276 therethrough. Tongue 2048f supports a gear 2050 between a proximal surface of tongue 2048f and a distal surface of U-shaped shoe 2046b of third segment 2046 so that teeth 2050a extending from gear 2050 are positioned between mating surfaces 2048h of each of the pair of arms 2048a, 2048b of fourth segment 2048 of distal end portion 2040 of outer tube 204.

Inner surfaces of gear 2050 define a channel 2050b therethrough. Inner surfaces of gear 2050 include a flat surface 2050c (see FIG. 15) that is supported on ledge 276f of distal firing shaft 276 such that gear 2050 and distal firing shaft 276 are keyed to one another.

Figure 16:
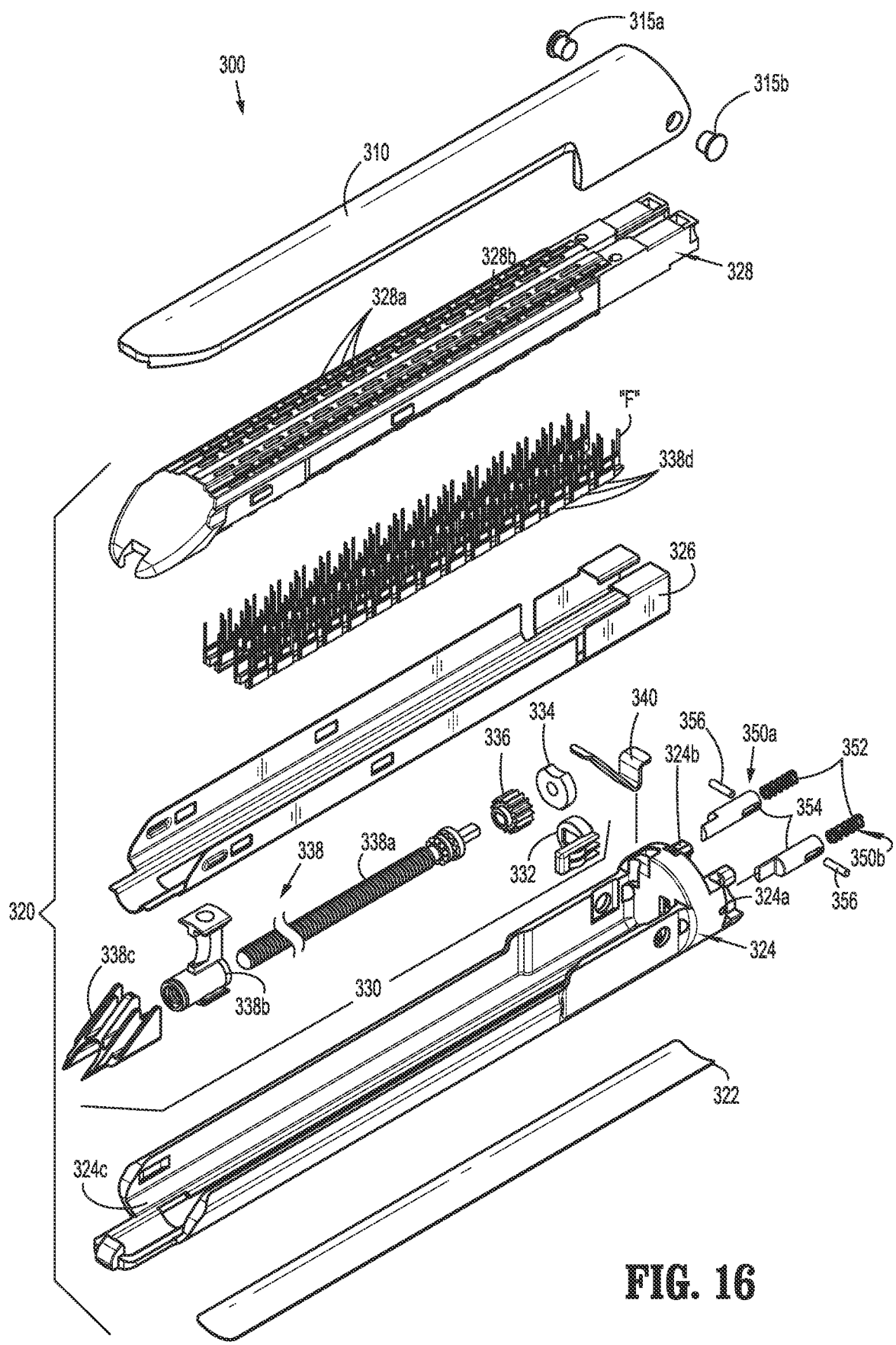
FIG. 16 is an enlarged, perspective view, with parts separated, of a surgical loading unit of the electromechanical surgical system of FIG. 1A.

Turning now to FIG. 16, loading unit 300 includes an anvil 310 and a cartridge assembly 320 that are pinned together by a pair of pins 315a, 315b and movable between open and closed conditions. Anvil 310 and cartridge assembly 320 cooperate to apply a plurality of linear rows of fasteners "F" (e.g., staples). In certain embodiments, the fasteners "F" are of various sizes, and, in certain embodiments, the fasteners "F" have various lengths or rows, e.g., about 30, 45 and 60 mm in length.

Cartridge assembly 320 includes a base 322 secured to a mounting portion 324, a frame portion 326, and a cartridge portion 328 defining a plurality of fastener retaining slots 328a and a knife slot 328b in a tissue engaging surface thereof. Mounting portion 324 has mating surfaces 324a, 324b on a proximal end thereof and defines a receiving channel 324c therein that supports frame portion 326, cartridge portion 328, and a fastener firing assembly 330 therein. Cartridge assembly 320 supports a biasing member 340 that engages anvil 310.

Fastener firing assembly 330 includes an electrical contact member 332 in electrical communication with the circuit board of surgical device 100 (FIG. 1A), a bearing member 334, a gear member 336 that engages gear 2050 of distal end portion 2040 of outer tube 204, and a screw assembly 338. Screw assembly 338 includes a lead screw 338a, a drive beam 338b, and an actuation sled 338c that is engagable with a plurality of pusher members 338d.

Cartridge assembly 320 also supports a pair of plunger assemblies 350a, 350b. Each of the pair of plunger assemblies 350a, 350b includes a spring 352, a plunger 354, and a pin 356 that secures each plunger assembly to mounting portion 324. Plunger assemblies 350a, 350b cooperate with the proximal end of cartridge portion 328 to facilitate securement of cartridge portion 328 within mounting portion 324.

Figure 17:
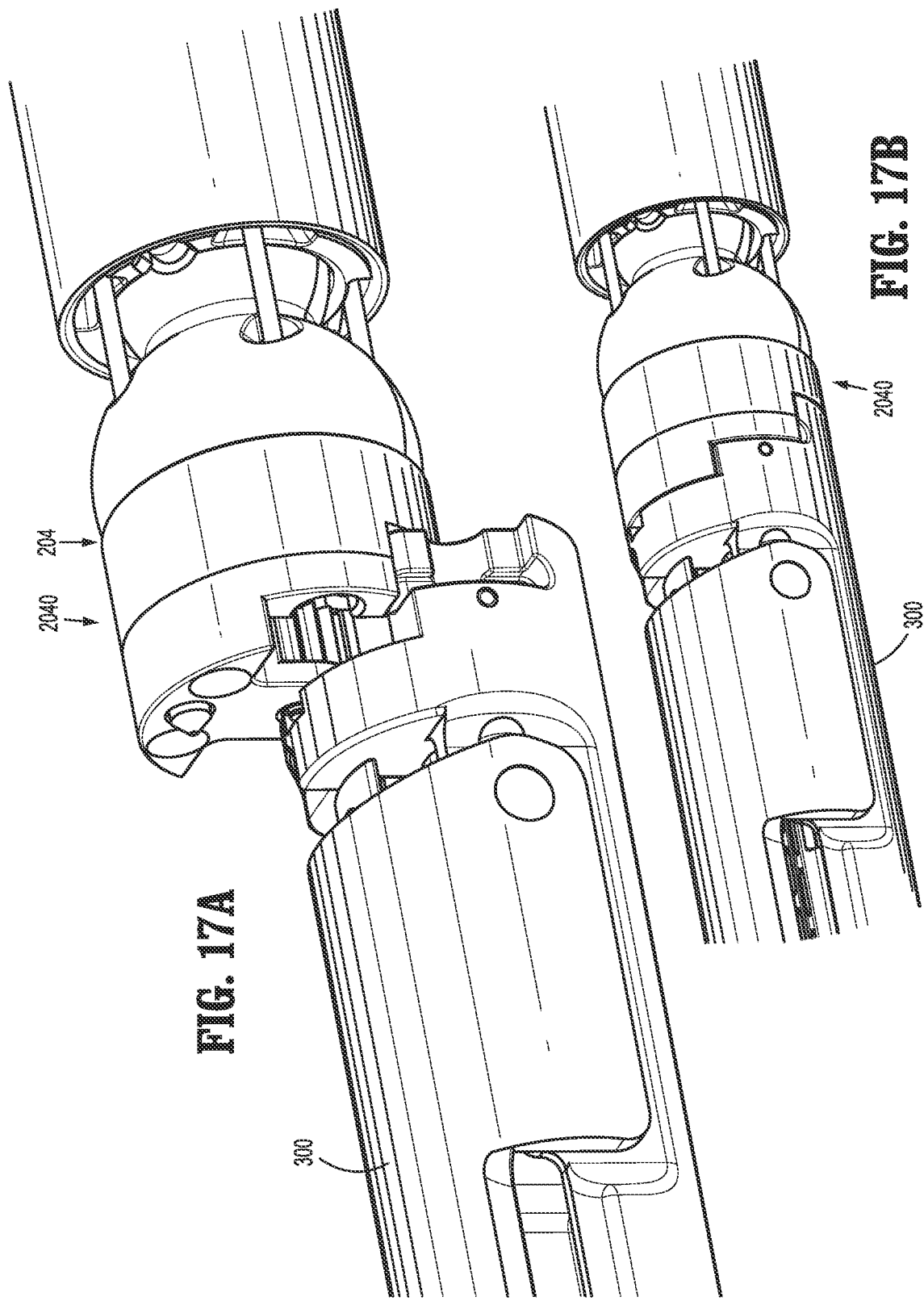
FIGS. 17A and 17B are progressive, side, perspective views illustrating a proximal portion of a surgical loading unit of the electromechanical surgical system of FIG. 1A being secured to the distal portion of the adapter assembly shown in FIG. 3.

In order to secure the proximal end of loading unit 300 to distal end portion 2040 of outer tube 204, the proximal end of loading unit 300 is aligned with distal end portion 2040 of outer tube 204 as seen in FIG. 17A so that the proximal end of loading unit 300 can be snapped together with distal end portion 2040 as seen in FIG. 17B. Referring also to FIGS. 10A and 16, mating surfaces 324a, 324b of loading unit 300 engage with mating surfaces 2048h of fourth segment 2048 so that the teeth of gear member 336 of loading unit 300 enmesh with the teeth of gear 2050.

In operation, actuation of knob 205d of joystick 205c causes rocker 205e to contact one or more of the directional switches 205b such that the direction of movement of the joystick 205c causes a corresponding movement in articulation assembly 230. Directional switches 205b are in operable communication with sensor(s) of articulation contact surface 105 to communicate with the circuit board, activate one or both of rotatable drive shafts 106a, 106c (due to an actuation of a motor (not shown) within handle housing 102), and effectuate rotation of threaded screw assembly 244 of one or both of the pair of sleeve assemblies 240a, 240b. In particular, rotation of each threaded screw assembly 244 is effectuated by virtue of rotational engagement between input socket 244b of one of the pair of sleeve assemblies 240a, 240b and one of rotatable drive shafts 106a, 106c. Rotation of threaded screw 244a axially moves the pair of threaded sleeves 246, 248 along the respective support shaft between an approximated condition (see FIG. 9) and a separated condition (see FIG. 4), as illustrated by lines "C1," "C2," "C3," and "C4" shown in FIG. 7. Relative axial movement of the pair of threaded sleeves 246, 248 proximally draws/retracts/tightens one/a first cable of one of the opposite pairs of cables (e.g., first cable 260a and fourth cable 260d being a first opposite pair of cables, and second cable 260b and third cable 260c being a second opposite pair of cables) of the plurality of cables 260 and distally lets out/extends/releases another/a second cable of one of the opposite pairs of cables to rotate/pivot/articulate gimbal 250.

Figure 18:
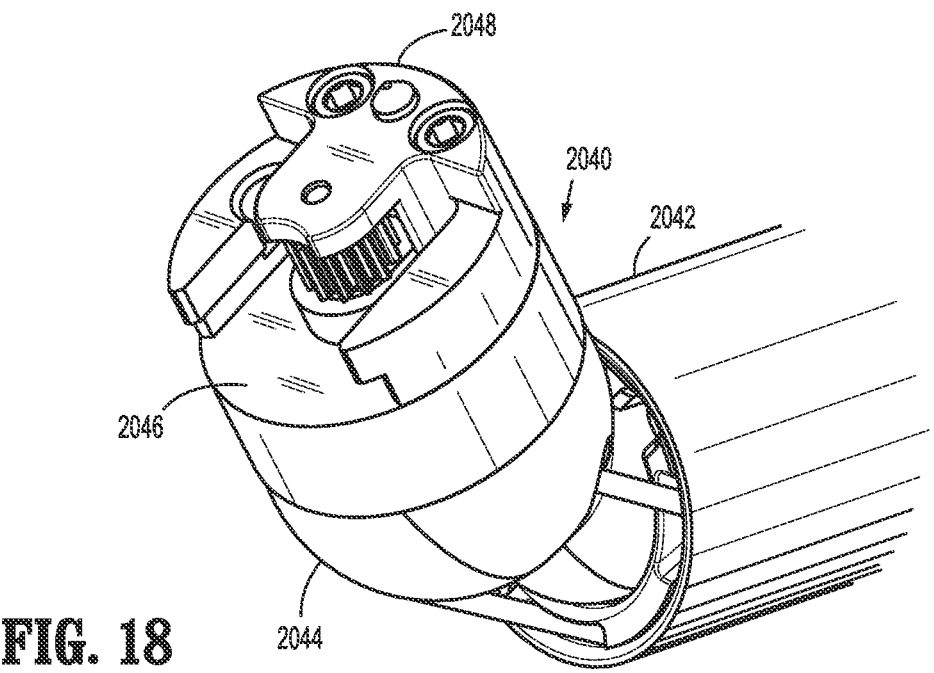
FIG. 18 is an enlarged, front, perspective view of the distal end portion of the adapter assembly of FIG. 3, the distal end portion of the adapter assembly being shown in an articulated condition.
Figure 19:
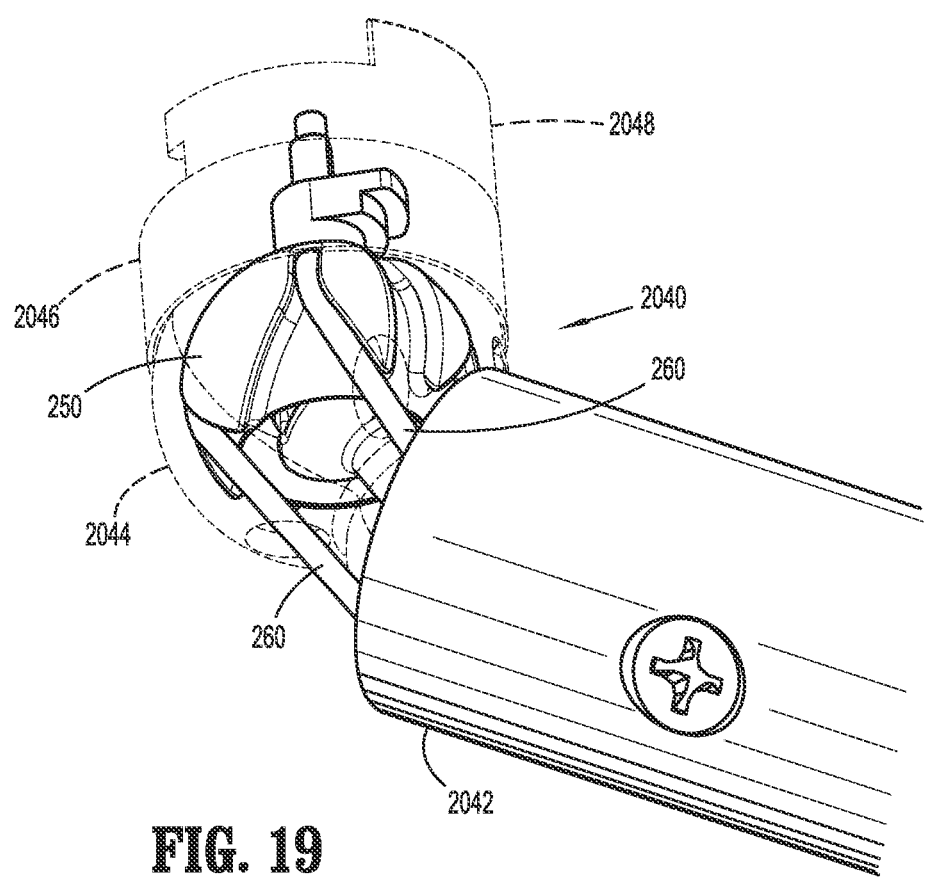
FIG. 19 is an enlarged, rear, perspective view of the distal end portion of the adapter assembly of FIG. 3 with portions thereof removed for clarity, the distal end portion of the adapter assembly being shown in the articulated condition.
Figure 20:
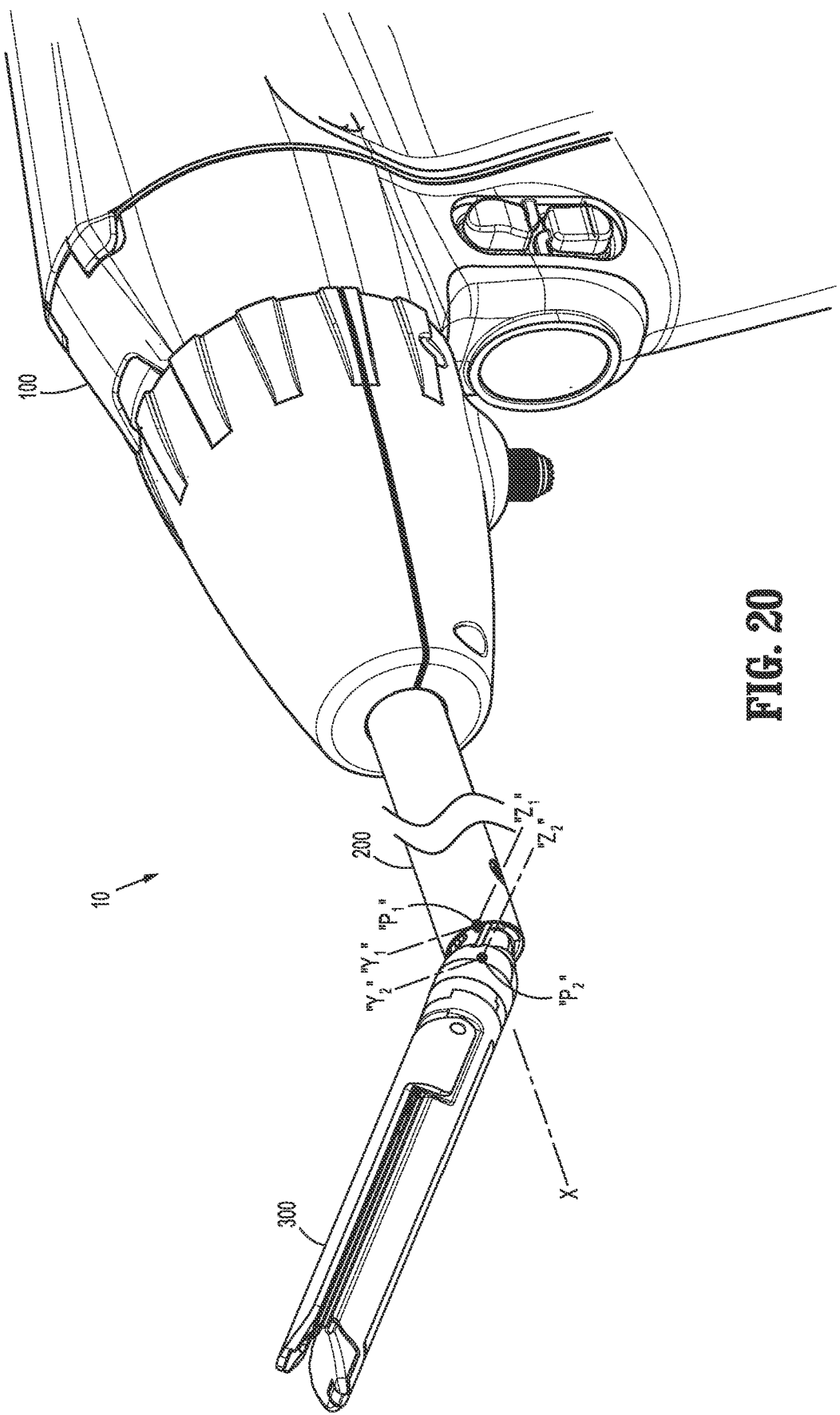
FIG. 20 is an enlarged, front, perspective view of a portion of the electromechanical surgical system of FIG. 1A, the surgical loading unit thereof being shown in the articulated condition.

Rotation of gimbal 250 causes a corresponding directional movement in proximal and distal universal joints 271, 273. As gimbal 250 rotates, distal portion 250b of gimbal 250 engages cylindrical body 2046a and/or U-shaped shoe 2046b of third segment 2046 to articulate distal end portion 2040 relative to outer tube 204 about longitudinal axis "X." Movement of distal end portion 2040 articulates loading unit 300 relative to outer tube 204 about longitudinal axis "X" in any direction (e.g., omni-directionally) as seen in FIGS. 18-20. More particularly, while longitudinally fixed to first segment 2042 of distal end portion 2040 of outer tube 204, loading unit 300, as well as second, third, and fourth segments 2044, 2046, 2048 of distal end portion 2040, can be articulated in any direction relative to the "X" axis. Specifically, loading unit 300 can articulate about the "$Y_1$" and/or the "$Z_1$" axes that extend from a proximal central point "$P_1$", and/or about the "$Y_2$" and/or the "$Z_2$" axes that extend from a distal central point "$P_2$" defined in distal end portion 2040 to position loading unit 300 at any desired orientation.

Tension/slack in one or more of the plurality of cables 260 may need to be adjusted, for example, before, during, and/or after one or more uses of system 10. To effectuate a tightening and/or loosening of slack/tension during manufacturing or re-conditioning, a tool (not shown) is connected to each screw 243 (see FIG. 4) to impart rotational movement to one or both of screws 243. Rotation of screws 243 causes one or both of the respective support shafts 242 to axially translate. Thus, rotation of one or both screws 243 adjusts tension in one or more of the plurality of cables 260 by moving one or both of the plurality of the pair of sleeve assemblies 240a, 240b as described above.

To fire the plurality of fasteners "F," actuation pad 108 of device 100 is actuated to rotate rotatable drive member 106b (due to an activation of a motor (not shown) within handle housing 102). Rotation of rotatable drive member 106b causes proximal firing shaft 274, central tube 275, and distal firing shaft 276 to rotate together about longitudinal axis "X" such that gear 2050 rotates gear 336 of loading unit 300. Rotation of gear 336 of loading unit 300 rotates lead screw 338a and enables drive beam 338b to axially advance along lead screw 338a and through longitudinal knife slot 328b by virtue of the threaded engagement between lead screw 338a and drive beam 338b. Drive beam 338b engages anvil 310 to maintain anvil and cartridge assembly 310, 320 in approximation. Distal advancement of drive beam 338b advances actuation sled 338c into engagement with the plurality of pusher members 328 and fires the plurality of fasteners "F" from the plurality of fastener retention slots 328a for forming against corresponding fastener forming pockets defined within anvil 310. Loading unit 300 can be reset and fastener cartridge 328 can be replaced so that loading unit 300 can then be re-fired as desired.

While certain embodiments have been described, other embodiments are possible.

Figure 21:
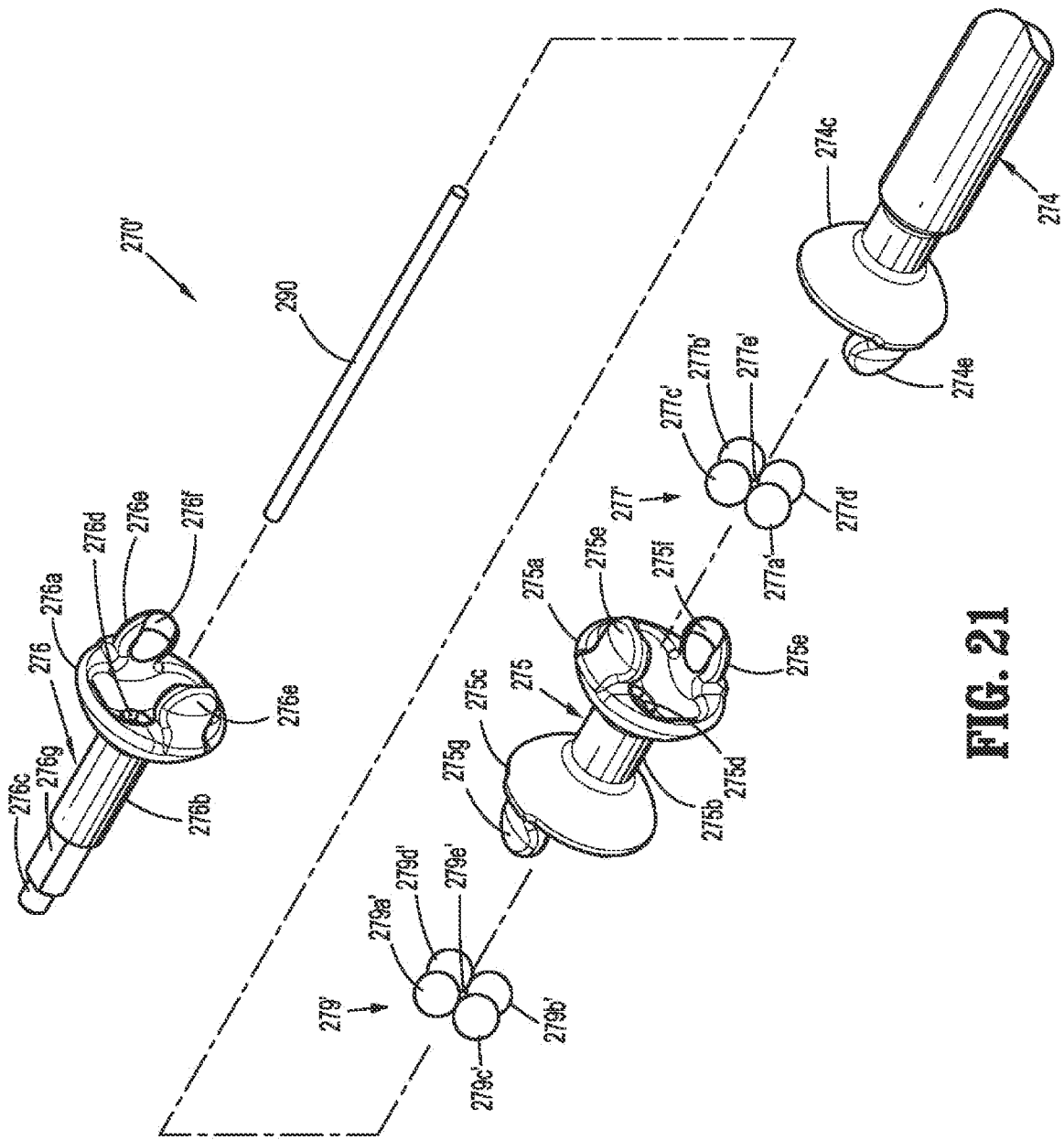
FIG. 21 is an enlarged, perspective view, with parts separated of a firing assembly of a distal portion of an adapter assembly in accordance with another embodiment of the present disclosure.

For example, other configurations of proximal and distal universal joints of the firing assembly of adapter assemblies of the present disclosure are additionally or alternatively possible. With reference now to FIG. 21, an embodiment of a firing assembly 270' is substantially similar to firing assembly 270 except that proximal and distal bearing assemblies 277' and 279' include a plurality of ball bearings 277a'-277d' and 279a'-279d', respectively, that are welded together and define an opening 277e' and 279e' therethrough. Accordingly, each ball bearing defines an outer arcuate surface that is complementary in shape with inner arcuate surfaces of proximal and distal tabs as described above.

Moreover, while proximal and distal tabs and proximal and distal bearing assemblies have been described as including complementary inner and outer arcuate surfaces, it should be appreciated that the tabs may include any surface geometry complementary with the geometry of the bearing assemblies to allow articulation of the joints about at least two axes as also described above.

Any of the components described herein may be fabricated from either metals, plastics, resins, composites or the like taking into consideration strength, durability, wearability, weight, resistance to corrosion, ease of manufacturing, cost of manufacturing, and the like.

In embodiments, any of the components described herein, such as the loading unit and/or adapter, can include one or more microchips, such as, for example a one-wire microchip (e.g., microchip model nos. DS2465, DS28E15, and/or DS2432, available from MAXIM INTEGRATED™, San Jose, CA) that electrically couple to the circuit board/controller of surgical device 100. Exemplary one-wire microchips are shown and described in U.S. Pat. No. 6,239,732, the entire content of which is incorporated herein by reference. Any of these chips can include encrypted authentication (e.g., SULU ID) and/or may be one wire compatible.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system comprising:
   an adapter assembly including:
      a housing;
      an outer tube extending distally from the housing along a longitudinal axis;
      a distal end portion extending distally from the outer tube;
      proximal and distal universal joints disposed within the distal end portion; and
      a gimbal disposed around the distal universal joint, the gimbal configured to rotate and cause a corresponding directional movement of at least one of the proximal or distal universal joints to articulate the distal end portion relative to the outer tube; and an end effector releasably connected to the distal end portion of the adapter assembly, wherein the distal end portion of the adapter assembly includes:

a first segment that is longitudinally fixed relative to the outer tube, the proximal universal joint rotatably coupled to the first segment;

a second segment having a proximal section disposed around the proximal universal joint and rotatably secured within the first segment, and a distal section disposed around the gimbal and the distal universal joint; and a third segment disposed over the distal section of the second segment, the distal section of the second segment rotatable therein.

2. The surgical system of claim 1, wherein the distal end portion of the adapter assembly includes a fourth segment secured to the third segment, the fourth segment configured to releasably engage the end effector.

3. The surgical system of claim 1, wherein the end effector includes an anvil and a cartridge assembly.

4. The surgical system of claim 1, wherein the adapter assembly includes a shaft assembly extending therethrough, the shaft assembly including:

a proximal shaft;

a central shaft intersecting the proximal shaft at the proximal universal joint; and a distal shaft intersecting the central shaft at the distal universal joint, the central shaft movable relative to the proximal shaft about the proximal universal joint and the distal shaft movable relative to the central shaft about the distal universal joint.

5. The surgical system of claim 4, wherein the proximal and central shafts are interconnected by a proximal bearing assembly, a distal portion of the proximal shaft and the proximal bearing assembly forming a first hinge of the proximal universal joint and a proximal portion of the central shaft and the proximal bearing assembly forming a second hinge of the proximal universal joint.

6. The surgical system of claim 4, wherein the central and distal shafts are interconnected by a distal bearing assembly, a distal portion of the central shaft and the distal bearing assembly forming a first hinge of the distal universal joint and a proximal portion of the distal shaft and the distal bearing assembly forming a second hinge of the distal universal joint.

7. The surgical system of claim 4, wherein a spring wire extends through the shaft assembly, the spring wire configured to bias the proximal, central, and distal shafts along the longitudinal axis of the outer tube and is bendable upon articulation of the gimbal.

8. The surgical system of claim 4, wherein the shaft assembly is configured to rotate relative to the gimbal.

9. The surgical system of claim 1, wherein the adapter assembly includes a plurality of cables secured to the gimbal, the plurality of cables configured to move and rotate the gimbal.

10. The surgical system of claim 9, wherein the adapter assembly includes sleeve assemblies secured to the plurality of cables, the sleeve assemblies configured to axially move and adjust tension on the plurality of cables to rotate the gimbal.

11. An adapter assembly for interconnecting an end effector and a surgical device, the adapter assembly comprising:

a housing;

an outer tube extending distally from the housing along a longitudinal axis;

a distal end portion extending distally from the outer tube;

proximal and distal universal joints disposed within the distal end portion; and a gimbal disposed around the distal universal joint, the gimbal configured to rotate and cause a corresponding directional movement of at least one of the proximal or distal universal joints to articulate the distal end portion relative to the outer tube, wherein the distal end portion includes:

a first segment that is longitudinally fixed relative to the outer tube, the proximal universal joint rotatably coupled to the first segment;

a second segment having a proximal section disposed around the proximal universal joint and rotatably secured within the first segment, and a distal section disposed around the gimbal and the distal universal joint; and a third segment disposed over the distal section of the second segment, the distal section of the second segment rotatable therein.

12. The adapter assembly of claim 11, wherein the distal end portion includes a fourth segment secured to the third segment, the fourth segment configured to releasably engage an end effector.

13. The adapter assembly of claim 11, further comprising:

a proximal shaft;

a central shaft intersecting the proximal shaft at the proximal universal joint; and a distal shaft intersecting the central shaft at the distal universal joint, the central shaft movable relative to the proximal shaft about the proximal universal joint and the distal shaft movable relative to the central shaft about the distal universal joint.

14. The adapter assembly of claim 11, further comprising sleeve assemblies and a plurality of cables interconnecting the sleeve assemblies and the gimbal, the sleeve assemblies configured to axially move and adjust tension on the plurality of cables to rotate the gimbal.

* * * * *